(12) United States Patent  (10) Patent No.: US 8,480,719 B2
Fortuna et al.  (45) Date of Patent: Jul. 9, 2013

(54) DEVICE AND METHOD FOR REGENERATIVE THERAPY BY HIGH INTENSITY LASER THERAPY

(75) Inventors: Damiano Fortuna, Florence (IT); Leonardo Masotti, Florence (IT)

(73) Assignee: El.En. S.p.A., Calenzano (IT)

( * ) Notice: Subject to any disclaimer, the term of this patent is extended or adjusted under 35 U.S.C. 154(b) by 0 days.

(21) Appl. No.: 13/048,627

(22) Filed: Mar. 15, 2011

(65) Prior Publication Data

US 2011/0208273 A1  Aug. 25, 2011

Related U.S. Application Data

(63) Continuation of application No. PCT/EP2009/061976, filed on Sep. 15, 2009.

(60) Provisional application No. 61/097,301, filed on Sep. 16, 2008, provisional application No. 61/097,251, filed on Sep. 16, 2008.

(51) Int. Cl.
*A61N 5/067* (2006.01)

(52) U.S. Cl.
USPC .................. 607/89; 128/898; 606/2

(58) Field of Classification Search
USPC .............. 128/898; 606/2–19; 607/88–94
See application file for complete search history.

(56) References Cited

U.S. PATENT DOCUMENTS

| | | | |
|---|---|---|---|
| 6,063,108 A | 5/2000 | Salansky et al. | |
| 6,235,015 B1* | 5/2001 | Mead et al. | 606/9 |
| 6,527,797 B1 | 3/2003 | Masotti et al. | |
| 6,637,437 B1* | 10/2003 | Hungerford et al. | 128/898 |
| 2001/0034517 A1 | 10/2001 | Masotti et al. | |
| 2004/0010300 A1 | 1/2004 | Masotti et al. | |
| 2004/0236318 A1 | 11/2004 | Davenport et al. | |
| 2007/0185552 A1 | 8/2007 | Masotti et al. | |
| 2007/0219605 A1* | 9/2007 | Yaroslavsky et al. | 607/100 |
| 2009/0069872 A1 | 3/2009 | Fortuna et al. | |
| 2010/0049322 A1* | 2/2010 | McKay | 623/16.11 |

FOREIGN PATENT DOCUMENTS

| | | |
|---|---|---|
| WO | WO 99/32193 A1 | 7/1999 |
| WO | WO 2004/007022 A1 | 1/2004 |
| WO | WO 2004/007023 A1 | 1/2004 |

OTHER PUBLICATIONS

"Notification of Transmittal of the International Search Report and the Written Opinion of the International Searching Authority, or the Declaration," mailed Mar. 23, 2010 for International Application No. PCT/EP2009/061976.

* cited by examiner

*Primary Examiner* — Henry M. Johnson, III
(74) *Attorney, Agent, or Firm* — Hamilton, Brook, Smith & Reynolds, P.C.

(57) ABSTRACT

A method of high intensity laser treatment for stimulating regeneration of living biological tissue in a patient by applying a pulsed laser beam to a skin of the patient in need of the treatment.

18 Claims, 10 Drawing Sheets

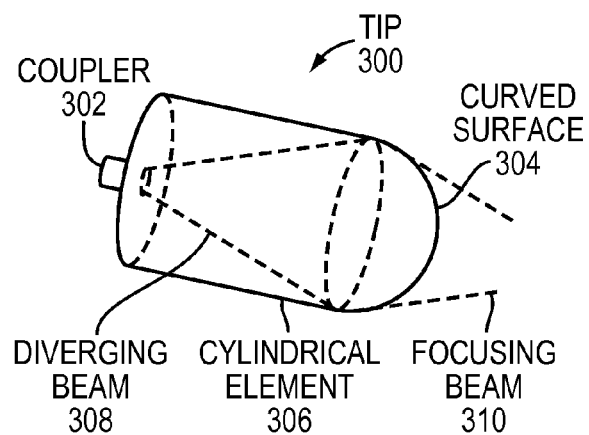
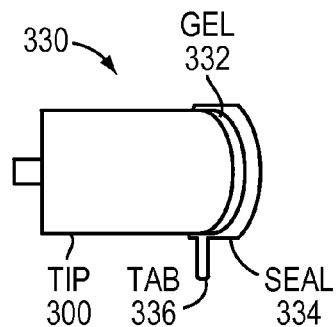
FIG. 3A
FIG. 3B
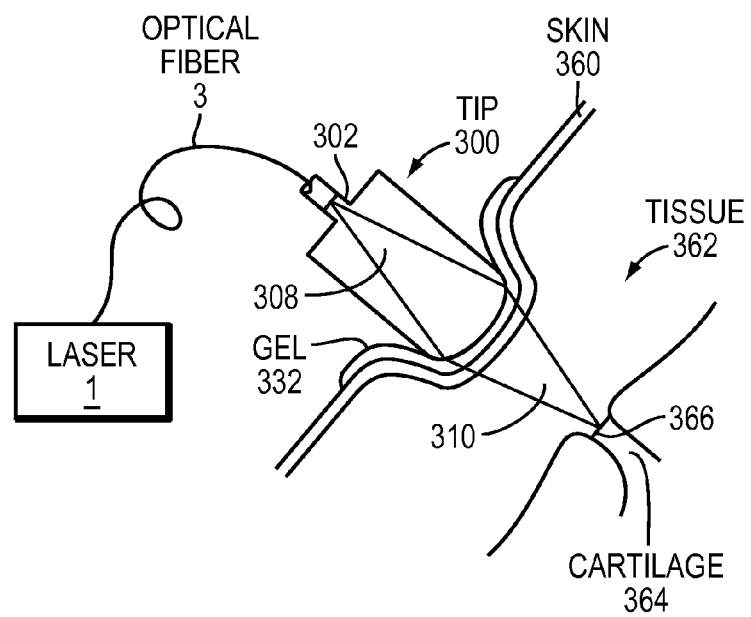
FIG. 3C

I) LASER PULSE INTENSITY
$c_j$) SPECIFIC HEAT
$\beta_j$) LINEAR EXPANSION COEFFICIENT
$K_j$) THERMAL CONDUCTIVITY
$\rho_j$) DENSITY
*$k_j$) THERMAL DIFFUSION COEFFICIENT
$v_j$) SOUND SPEED
$\alpha$) OPTICAL ABSORPTION COEFFICIENT OF THE TISSUE
z) DEPTH
t) TIME

DEVICE AND METHOD FOR REGENERATIVE THERAPY BY HIGH INTENSITY LASER THERAPY

RELATED APPLICATIONS

This application is a continuation of International Application No. PCT/EP2009/061976, which designated the United States and was filed on Sep. 15, 2009, published in English, which claims the benefit of U.S. Provisional Application No. 61/097,301, filed on Sep. 16, 2008 and U.S. Provisional Application No. 61/097,251, filed on Sep. 16, 2008.

The entire teachings of the above applications are incorporated herein by reference.

BACKGROUND OF THE INVENTION

Since their discovery lasers have been advocated as alternatives to conventional clinical methods for a wide range of medical applications. For many years high-powered and highly focused lasers have been used to cut and separate tissue in many surgical techniques. More recently, therapeutic and biostimulating properties of laser radiation were discovered. It is believed that laser radiation stimulates several metabolic processes, including cell division, synthesis of hemoglobin, collagen and other proteins, leukocyte activity, production of macrophage cells and wound healing. In this case the laser radiation acts as a stimulating agent on the cell activity and activates therewith the body's own healing capability.

Laser therapy is often used to give relief for both acute and chronic pain, resolve inflammation, increase the speed, quality and tensile strength of tissue repair, resolve infection and improve the function of damaged neurological tissue. This therapy is based on the application of narrow spectral width light over injuries or lesions to stimulate healing within those tissues. Treatment with laser beams is painless and causes neither a macrochemical change nor damage in the tissue.

Up to now the actual mechanism of action underlying the laser effects has not yet been fully understood. According to one theory, the energy of laser radiation is incorporated in natural processes in a manner similar to that by which the "quanta" of light are incorporated in the chain of reactions of plant photosynthesis. Another theory is based on the assumption that cells and tissues have a certain reserve of free charge and are surrounded by a particular biological field such that the interconnections among organism, organs, apparatus and tissues are not determined by mechanisms of humeral, nervous and chemical regulations only, but also by more complex energetic connections.

The lack of understanding of the basic mechanisms underlying the effects of laser application resulted in a diverse range of therapeutic devices and protocols using laser in very different ways and with different wavelength. Several U.S. patents have been granted for different apparatus and methods based on the laser application for therapeutic treatment of living tissue by laser irradiation. Among them the following are particularly relevant: U.S. Pat. No. 4,671,258 to Walker; U.S. Pat. No. 4,930,504 to Diamantopoulos et al.; U.S. Pat. No. 4,931,053 to L'Esperance, Jr.; U.S. Pat. Nos. 5,445,146 and 5,951,596 to Bellinger; and U.S. Pat. No. 5,755,752 to Segal, all of which are incorporated herein by reference in their entireties.

All the above mentioned patents, as well as most works in this field, refer to use of lasers at "low" or "medium" power level. This kind of therapy is now popularly referred to LLLT (Low Level Laser Therapy) or LILT (Low Intensity Laser Therapy). The power range used in LLLT is between few mW and 1,000 mW.

LLLT has become a popular treatment in a variety of medical disciplines. This therapy is used with some success but results are obtained only slowly and are inconsistent. The degree of therapeutic effect achieved is variable and heavily depends upon the dosage of luminous wave, exposure rhythm, and the distance of the treated tissue from the laser source. Applications of several minutes are repeated at intervals of several days and often repeated for months.

SUMMARY OF THE INVENTION

Accordingly, embodiments of the present invention include an apparatus and method for high intensity laser therapy (HILT). Example methods include applying a pulsed laser beam to the tissue, where the laser beam has a peak intensity fluence of 0.1 $(J/cm^3)^2$ to 1.0 $(J/cm^3)^2$. The peak intensity fluence (PIF) is defined by:

$$PIF = I_p \tau_{on} \cdot \frac{E}{10 r^3} \alpha \cdot \frac{\tau_{off}}{(\tau_{on} + \tau_{off})}$$

where $I_p$ is the peak intensity of a pulse of the pulsed laser beam, E is the energy of the pulse, $\tau_{on}$ is the duration of the pulse, $\tau_{off}$ is the duration between pulses, r is the radius of a spot formed by the pulsed laser beam on the patient, and $\alpha$ is the water absorption coefficient ($cm^{-1}$) at the wavelength $\lambda$ of the pulsed laser beam.

In preferred embodiments, the peak power of the pulse is between 400 W and 50 kW; the duration of the pulse is from 1 microseconds to 500 microseconds; the duty cycle of the pulsed laser beam is from 0.01% to 0.5%; and the diameter of the spot formed by the pulsed laser beam on the tissue under treatment is from 1 millimeter to 20 millimeters. Other embodiments may involve alternative combinations of parameters, provided that the PIF remains within acceptable ranges.

The pulsed laser beam may be applied either percutaneously or transcutaneously. For example, it may be applied transcutaneously via an optical fiber inserted through the patient's skin. The spot formed on the tissue under treatment may have a diameter of between about 1 mm and about 20 mm, or between about 2.5 mm and about 20 mm. The area of the spot may be greater than 0.05 $cm^2$, or it may be between about 0.05 $cm^2$ and about 3.14 $cm^2$. The optical fiber used to project the spot may have an external diameter of between about 300 μm and about 1.5 mm, and may be 0.6 mm or 1.0 mm. A conical emitting tip coupled to the optical fiber may have a height of between about 0.35 cm to 1.00 cm, of 0.50 cm, or of 0.80 cm; the cone-shaped tip may have an area between about 0.014 $cm^2$ and about 0.54 $cm^2$, or about 0.058 $cm^2$, or about 0.23 $cm^2$. The conical tip (hand probe) may have a diameter of 2.5 mm or greater.

The pulsed laser beam may be applied percutaneously with an optical tip in contact with the patient's skin. Example optical tips include an optical fiber coupler and a focusing element coupled to the optical fiber coupler that focuses the pulsed laser beam to a spot in the tissue at a distance of between about 0.5 cm to about 10 cm in the tissue. Example optical tips may be made of plexiglass, plastic, or tempered glass. Embodiments of the optical tip may be disposable and may come in sealed packages.

The focusing element, which is at least partially covered in gel, may include a cylindrical element and a curved surface. The cylindrical element may be between about 3 cm long and about 4 cm long and has a diameter of between about 1.5 cm and 2.5 cm, and can be pushed against the skin to compress tissue between the skin and the tissue being treated. The curved surface may have a diameter of about 2 cm and a radius of curvature of between about 10 mm and about 100 mm.

The gel transmits light at the wavelength of the pulsed laser beam and reduces optical impedance mismatch between the optical tip and the skin at the wavelength of the pulsed laser beam. The gel also lubricates the area of contact between the optical tip and the skin. In addition, it cools the skin during application of the pulsed laser beam. The gel and the optical tip may also be pre-cooled or pre-refrigerated to help maintain a low temperature at the skin interface during treatment.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 3A-3C are schematic diagrams of an optical tip suitable for use with the device shown in FIG. 2.

DETAILED DESCRIPTION OF THE INVENTION

Figure 1:
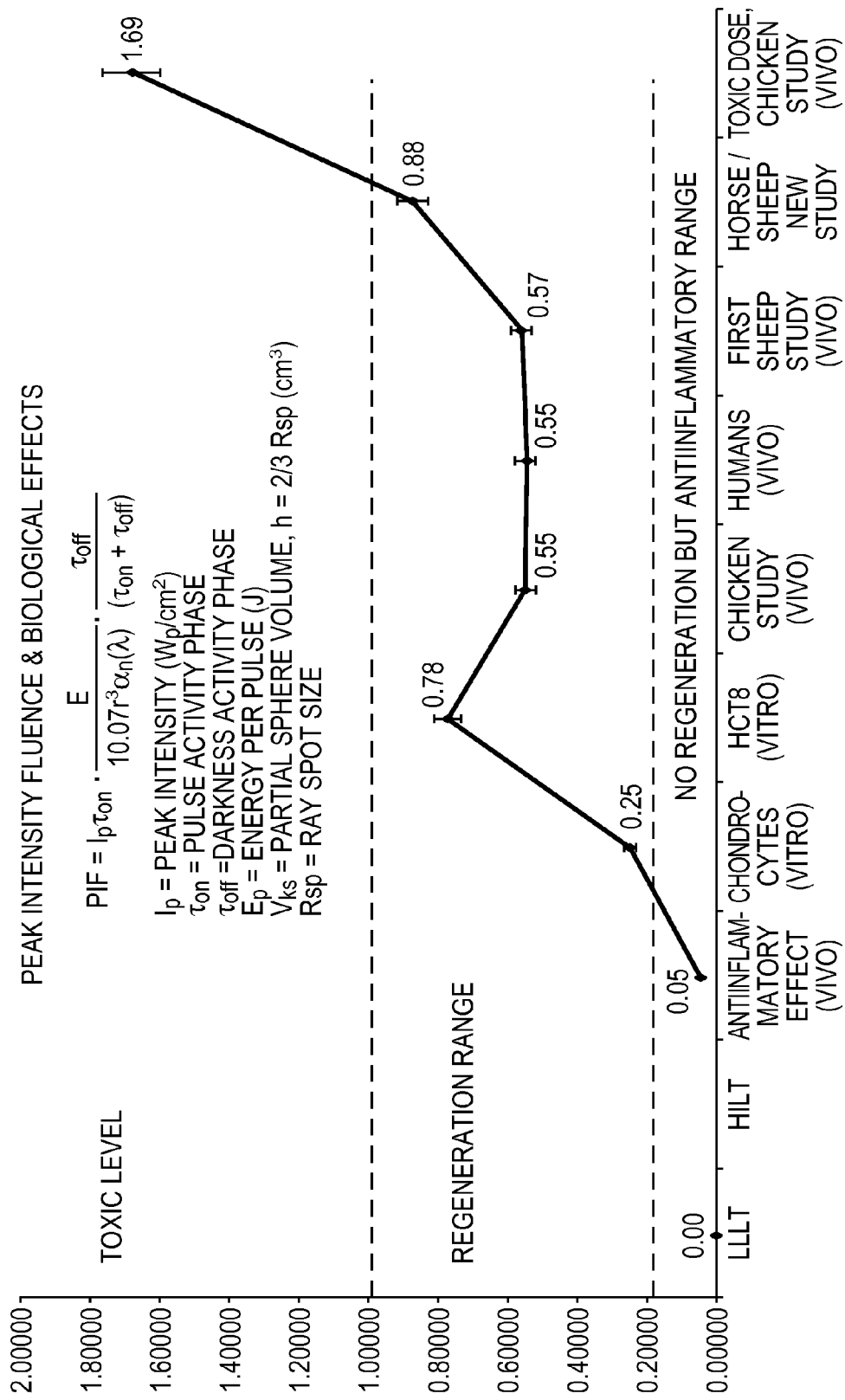
FIG. 1 is a plot of peak intensity fluence (PIF) versus biological effect.

A description of example embodiments of the invention follows.

The teachings of all patents, published applications and references cited herein are incorporated by reference in their entirety.

In view of the unsatisfactory results obtained with LLLT, there is a need for a more efficient device and a better method of laser treatment with which faster and more consistently reproducible results can be obtained. Specifically, LLLT can only produce either the photochemical effect or the photochemical and photothermal effects but not all three. Pulsed emission must be used to induce the photomechanical effect with the photochemical and photothermal effects.

Provided herein are a protocol of therapy and a relevant device for high intensity last therapy (HILT) radiation for noninvasive regenerative therapy. Other, similar methods of and devices for laser therapy are disclosed in U.S. application Ser. No. 11/099,216, filed Apr. 5, 2005, by Cho and Masotti; U.S. application Ser. No. 11/704,710, filed Feb. 9, 2007, by Cho and Masotti; and U.S. application Ser. No. 12/283,612, filed Sep. 12, 2008, by Masotti and Fortuna.

Peak Intensity Fluence (PIF)

HILT can induce photomechanical, photothermal, and photochemical effects by means of pulsed laser emission characterized by a particular peak intensity fluence (PIF). PIF defines pulse emission characteristics better than average power density, which does not supply sufficient information about the temporal and spatial shapes of the pulses. Peak intensity (the ratio of the peak power to the spot area) gives an idea of the 3D spatial distribution, but it fails to provide information regarding the energetic content of the pulse and its time distribution. The fluence (energetic content divided by the spot size) indicates the photon density in time but does not give the intensity, or photon density in space. (For example, the same fluence may be common to an infinite number of different pulses that have different peak powers and pulse durations $\tau_{on}$).

We therefore condensed the peak intensity together with the pulse emission time to define PIF, which includes both a spatial component and a time component. PIF may be expressed as $$PIF = I_p \tau_{on} \left(\frac{E_p}{V_{ks}}\right) \alpha \left(\frac{\tau_{off}}{T}\right)$$

which can be considered as comprising the three elements described below.

A first element, which defines the intensity of light within the target region, is the two-dimensional energy per pulse, $I_p \tau_{on}$, where $I_p$ is the Peak Intensity ($W_p/cm^2$), or peak power ($W_p$), divided by the surface area of the spot ($cm^2$), and $\tau_{on}$ is the pulse duration.

The second element defines a three-dimensional relationship between the pulse and the irradiated tissue. The second element, $(E_p/V_{ks})\alpha$, is the energy per pulse, $E_p$, divided by the irradiated tissue volume $V_{ks}$, and $\alpha$ is the absorption coefficient of water. The volume $V_{ks}$ may be approximated as a fraction of the volume of the sphere segment being radiated by the laser, $V_{ks}=10.07 \cdot r^3$, where r is the spot size radius. The distance from the origin of the sphere to the center of the spot, h, is about two-thirds the radius of the spot.

Because the ratio $E_p/V_{ks}$ should be considered in relation to the wavelength, $\lambda$, the volume $V_{ks}$ may be treated having an absorption roughly equal to the water absorption coefficient $\alpha$, which varies in relation to $\lambda$. For example, at $\lambda=1064$ nm, $\alpha=2.29$ cm$^{-1}$, while at $\lambda=980$ nm, $\alpha=3.52$ cm$^{-1}$.

The third element of the formula, $\tau_{off}/T$, describes the relationship between the pulse off period, or dark phase, $\tau_{off}$, and the total pulse period, $T=\tau_{on}+\tau_{off}$. The PIF can also be written in terms of the pulse on and off periods, $$PIF = \left(\frac{J}{cm^3}\right)^2 = I_p \tau_{on} \cdot \frac{E}{10.07 r^3} \alpha \cdot \frac{\tau_{off}}{(\tau_{on} + \tau_{off})}$$

(This relationship can also be characterized by a pulse duty cycle, which is the ratio of the pulse on time to the pulse period, $\tau_{on}/T$.) The dark phase is important for maintaining the tissue temperature, as overheating the tissue may cause thermal damage.

One aspect of the present invention is induction of the photomechanical effect responsible for the physiological cellular differentiation. The photomechanical effect can be induced for laser pulses with temporal and spatial shapes tuned for a given spot size. If the intensity of the pulse is too low, there is little or no photomechanical effect. If the pulse intensity is too high, the pulse may be toxic to the tissue.

To obtain a regenerative effect on the tissues and a cytoproliferative effect on the cell cultures, pulses provided with HILT have a Peak Intensity Fluence (PIF) of between about 0.1 $(J/cm^3)^2$ and about 1.0 $(J/cm^3)^2$. In an alternative embodiment, the PIF may be between 0.2 $(J/cm^3)^2$ and 0.88 $(J/cm^3)^2$. PIFs over 1.0 $(J/cm^3)^2$ may be toxic. PIFs below 0.1 may have only an anti-inflammatory effect. In contrast, LLLT systems used for pain management have a PIF between 0.0 (i.e., the beams are continuous-wave beams) and 0.0015 $(J/cm^3)^2$, or approximately 100 to 1000 times lower then the PIF for HILT.

FIG. 1 is a graph that shows the correlation between the characteristics of the HILT pulse, expressed in PIF $(J/cm^3)^2$, and the biological effects observed in experimental trials. Each data point represents the PIF of a pulsed laser beam applied in a particular setting, e.g., to chickens, sheep, or humans in vivo. The vertical lines extending from each point are error bars. The dashed horizontal lines indicate a range of acceptable PIFs for tissue regeneration: from just under 0.2 $(J/cm^3)^2$ to just under 1.0 $(J/cm^3)^2$. Below 0.1 $(J/cm^3)^2$, there may be just an anti-inflammatory effect and not a regenerative effect; whereas for PIFs exceeding 1.0 $(J/cm^3)^2$ there may be a histo-toxic effect.

Pulsed Laser Beam Parameters

Sufficient PIFs may be achieved by varying pulsed laser beam parameters within a wide range of acceptable values, provided that the PIF remains within the range of 0.1 $(J/cm^3)^2$ to 1.0 $(J/cm^3)^2$. Different combinations of parameters may be expressed in different ways; for example, peak intensity may also be expressed in terms of peak power and spot size. Similarly, the pulse repetition frequency and duty cycles are fixed by the pulse duration and the time between pulses.

Short pulse durations may avoid accumulation of thermal energy in the tissue. The thermal energy impacting on the tissue during one pulse is dissipated before the next pulse arrives. Temperature control of the tissue is thus obtained. Therefore, embodiments of the present invention may employ pulsed laser beams with a pulse duration between 1 microsecond to 500 microseconds. Similarly, the pulsed laser beam has a pulse repetition frequency between 0.2 Hz and 100 Hz. Such low values of the pulse frequency allows optimal thermal dissipation.

The duty cycle indicates the ratio between τ-on and T in a laser pulse, where T=τ-on+τ-off, and is the total duration of a pulse cycle, τ-on is the time interval during which the laser beam is on and τ-off is the time interval during which the laser beam is off. The shorter the τ-on time interval, the lower the duty cycle. A low duty cycle in combination with a high mean power value results in very high peak power values per pulse. Low duty cycles allow sufficient time between subsequent τ-on periods during which heat can be removed from the treated tissue, avoiding tissue damages, in spite of the extremely high peak power values achieved during each τ-on period. Accordingly, the pulsed laser beam may have a duty cycle of 0.01% to 0.5%.

The pulsed laser beam may be de-focused to generate a spot of substantially circular form, with a diameter between 4 and 20 mm. Alternatively, the pulsed laser beam has a spot on the skin with a diameter between 5 and 7 mm. The radius of the focused spot on the tissue being treated, e.g., cartilage, may be from 0.12 centimeters to 1 centimeter, for a spot area of between 0.05 $cm^2$ and 3.14 $cm^2$. Contrary to these spot sizes generated by a de-focused laser beam according to the present invention, the prior art methods require focusing means in order to achieve the desired power density with the low power levels suggested therein.

As mentioned above, the intensity (W/$cm^2$) of the pulsed laser beam relates to the power of the laser beam at the surface of the body being treated (spot size). By increasing the spot size on the surface, there is a consequent reduction in the power density. Therefore, in order to obtain suitable power densities to exert photomechanical effect on the tissues and/or cells being treated, especially when the spot sizes are large, laser lights of very high powers are preferably used. According to still another embodiment of the present invention, the pulsed laser beam has a peak power of at least 35 kW; at least 1 kW; or between 400 W and 50 kW. Similarly, the pulsed laser beam has an energy per pulse between 0.03 and 10 Joules, or, more preferably, between 0.2 and 2 Joules. The pulsed laser beam may also have a peak intensity between 5 kW/$cm^2$ and 25 kW/$cm^2$.

It will be clear from the above that, especially when high peak power levels are used, such as for the treatment of chronic degenerative pathologies, strict control of the treatment conditions are important. The peak power should be as high as possibly compatible with the need to avoid thermal damage of the tissues. The actual operating conditions strongly depend upon the phototype (skin color) of the patient under treatment. According to a further aspect of the present invention, the skin temperature can advantageously be detected in a continuous or discontinuous manner, such that the actual skin temperature is kept under control. The irradiation conditions are set such as to have the most effective irradiation (i.e., the deepest penetration and the highest power levels), without nevertheless exceeding threshold temperature values, e.g. 40° C. or 42° C. of the skin temperature.

This can be achieved by a temperature sensor arranged on a handpiece, such as the handpiece shown in FIG. 2 (described below). A photodetector for determining the skin color (phototype) of the patient under treatment could also be combined to the handpiece. In addition to providing proper control during treatment, the temperature sensor and photodetector are useful in order to determine the quantity of energy which is absorbed by the tissue and transformed into heat or else reflected by the skin. Knowing the total energy emitted by the source and impacting the skin, the value of the energy actually reaching the deeply located tissues to be treated can be determined with sufficient precision.

It should be appreciated that the peak power and the average power of the laser light of the present invention are greater than those used in the prior art therapeutic methods, in particular those disclosed in the previously cited U.S. patents. On the other hand, the pulse duration of the laser light of the present invention is much shorter.

HILT Apparatus

The present invention also relates to a device for laser therapy comprising a first laser source which produces a single therapeutic laser radiation, a first conveying means for conveying the laser energy to a hand unit, and optical defocusing means for defocusing the laser beam, which are positioned in the path of the laser beam According to a preferred embodiment, the conveying means is formed by an optical fiber, in front of the output end of which the optical defocusing means are arranged. When using the optical fiber, the emitting surface of the tip may be larger than 0.05 $cm^2$ to avoid damaging the tissue around the tip.

The hand unit, where the laser optical path ends and the defocusing means are arranged, can be held by the operator at the appropriate distance from the epidermis of the patient undergoing treatment. In order to make use safer and easier for the operator, however, the hand unit is in a preferred embodiment provided with a distance element to hold said optical means of defocusing at the predetermined distance from the body of a patient to whom the treatment is being applied, avoiding the necessity of determining and manually maintaining the optimal distance.

Again for the purpose of facilitating use of the device, it can be provided with a second laser source which emits at a wavelength in the visible range, and optical fiber or equivalent means for conveying the laser beam generated by said second source towards the hand unit. This second laser source is only a marker and it has no therapeutic properties.

Figure 2:
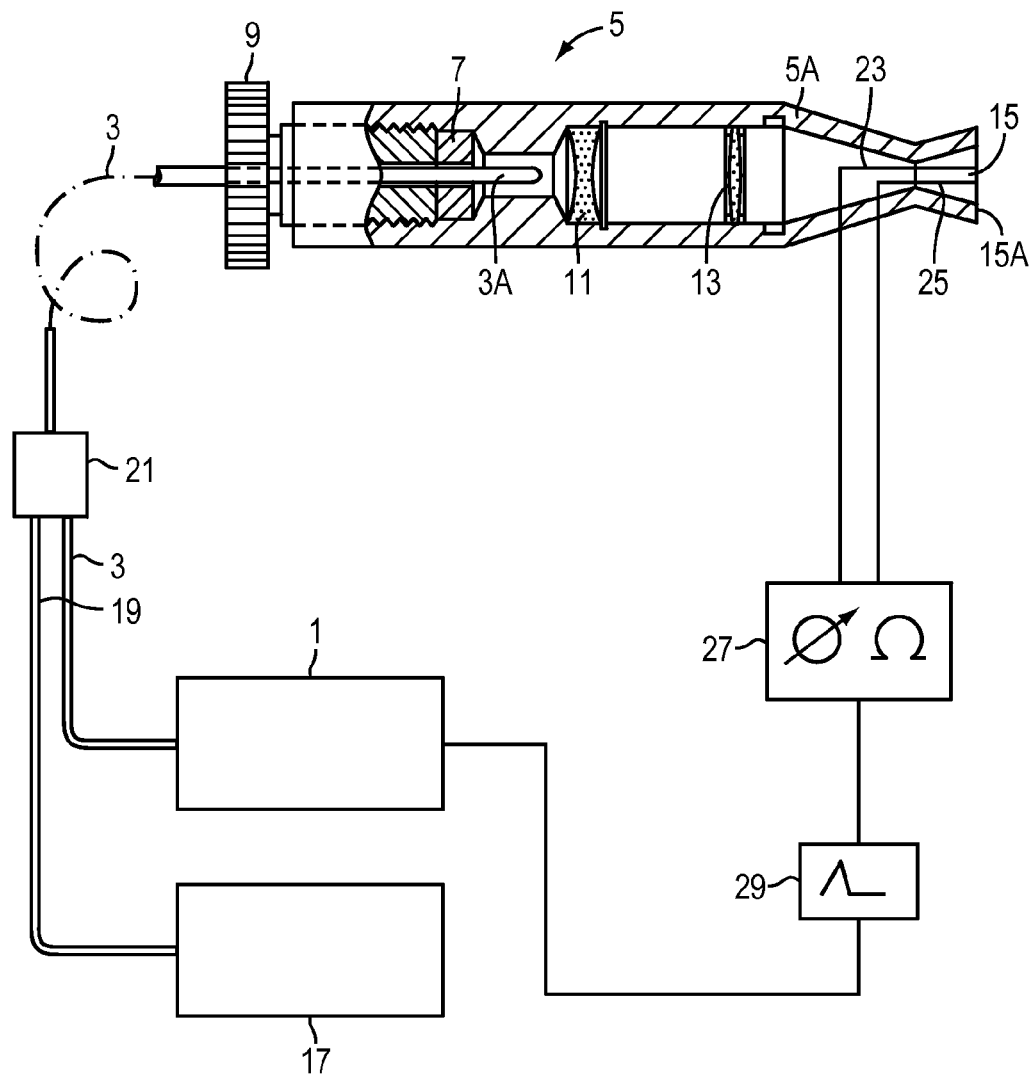
FIG. 2 shows the hand unit of the device and, diagrammatically, the laser sources and the control systems.

In FIG. 2, 1 indicates a laser source, preferably a Nd:YAG laser with emission at 1.064 micrometers, connected by means of an optical fiber 3 to a hand unit 5. Inside the hand unit, the output end 3A of the optical fiber 3 is fixed by means of an elastic sleeve 7 and clamping nut 9. Arranged facing the end 3A of the optical fiber 3 is a defocusing optic 11, 13.

The hand unit 5 ends in a converging end 5A to which is fixed a distance piece 15 with a surface 15A which is brought into contact with the epidermis E of the patient to whom the treatment is being applied. In this way, the defocusing optic 11, 13 is always held at a predetermined distance from the epidermis. In this way, once fixed, the energy is determined only by the energy density.

A second laser source 17 which emits continuously at a wavelength in the visible range introduces a laser beam into the fiber 3 by means of an auxiliary optical fiber 19, a connector 21 and a mixer. As an alternative and equivalent, the second laser source can send the laser beam into a known device for coaxial mixing of the two laser beams. The two beams made coaxial are then sent to a known device for introduction into the fiber.

In this manner, the treatment zone is illuminated and can be seen by the operator in the presence of the distance piece 15 also if this is open or made of a transparent material.

Associated with the distance piece 15 are two electrodes 23, 25 connected to a resistance measuring device 27. This measures the resistance of the epidermis in the region of the zone of application of the hand unit 5 and, by means of a trigger signal generator 29, generates a control signal for the laser source 1 in such a manner that the latter emits pulses at the frequency and of the duration desired when the hand unit 5 is in the region of the trigger point, where the resistance measured by the measuring device 27 is low.

The features of the laser emission from source 1 can be as follows. During each period T of the pulsed laser emission a pulse of duration τ is generated followed by an "off" interval. As stated above, the ratio D between the duration of the pulse and the period T is the duty cycle (D=τ/T) of the laser emission. The peak power is designated Pp, and is linked to the mean or average power per pulse Pm via the period T and the duty cycle D as indicated above.

According to an embodiment of the invention, high power-pulsed laser beams are generated by a solid state laser source, i.e., a laser source formed by a doped mono-crystal structure. A suitable solid state laser source is a Nd:YAG laser. This laser can emit a sufficiently high-power pulsed laser and has an emission wavelength of 1064 nm, a particularly advantageous wavelength because said radiation can be transmitted through biological tissues of interest in the present application and achieve in-depth cartilage structures on which tissue regeneration is required.

A pulse with characteristics according to the present invention is preferably obtained with a solid state source (e.g., Nd:YAG). It is not physically obtainable with a diode laser or with LEDs. Semi-conductor lasers, lamps or LEDs are not capable of emitting pulses with the characteristics according to the present invention.

The dimension of the spot generated by the laser beam on the skin of the patient being treated depends on the optical features of the defocusing means and on the distance between the optical defocusing means and the skin. The power density, i.e., the power per surface being a critical value, the dimension of the spot is an important parameter characterizing the method of treatment. This is selected such that the power density falls within the range indicated above, depending upon the particular application.

Optical Tip

FIGS. 3A, 3B, and 3C show perspective and schematic views of an optical tip 300 suitable for use with the laser source 1 shown in FIG. 2. As shown in FIG. 3A, the tip 300 includes an optical fiber coupler 302 connected to a focusing element, which includes a cylindrical element 306 and a curved surface 304. The curved surface 304 transforms a diverging beam 308 exiting the coupler 302 into a focusing beam 310 whose plane of focus is determined, in part, by the curved surface's radius of curvature.

Example optical tips 300, which may be disposable, are made of transparent solid plexiglass rods or pre-cast plastic. Non-disposable tips 300 may be made of tempered glass or plastic. The cylindrical element 300 may have a diameter of about 2 cm and a length of 3-4 cm. The curved surface 304 may have a radius of curvature between 10 mm and 100 mm. The coupler may be integral with or connected to the focusing element. Alternative tips 300 may use zone plates instead of curved surfaces 304 to focus diverging beams 308.

FIG. 3B shows a perspective view of a optical tip 300 in a sealed package 330. A seal 334 prevents a gel 332 coated over at least part of the curved surface 304 from drying out or becoming contaminated. Preferred gels 332 are transparent at the treatment wavelength; examples include generic ultrasound gels. The seal 334, which may cover the entire tip 300 or just the gel-coated portion of the tip 300, can be removed by pulling on the tab 336. The tip 300 and the sealed package 330 can be disposed of after use.

FIG. 3C is a schematic diagram of percutaneous treatment of cartilage 364 using an optical tip 300. An optical fiber 3 couples a laser source 1 to the tip 300 via the coupler 302. The tip's curved surface 304 focuses the diverging beam 308 from the fiber to a treatment area 366 on the cartilage. Depending on the tip's radius of curvature and the index of tissue 362, skin 360, and gel 332 between the tip 300 and the cartilage 364, the focal length in tissue may be between 0.5 cm to about 10 cm in tissue 362.

The gel 332 transmits light at the treatment wavelength, thereby reducing any optical impedance mismatch between the tip 300 and the skin 360. The gel 332 also lubricates and cools the skin 362, preventing thermal damage. The skin 362 can also be cooled with a tip 300 that is refrigerated or cooled either during or before treatment.

Scanning Delivery System

Automatic or manual scanning delivery systems may be used to effectively and safely deliver pulsed laser beams to treatments areas. Scanning is useful for treating surface areas larger than the irradiating surface area of the laser (spot size of the handpiece or emission surface of the optic fiber). Scan parameters, such as the dwell time on each location in the treatment area, may be fixed by the desired dose, pulse period, and pulse repetition rate. As long as the dwell time remains within acceptable ranges, these should not be any risk of excessive heating or therapeutic inefficiency. Thus, scanning also contributes to controlling tissue temperature.

Figure 4A:
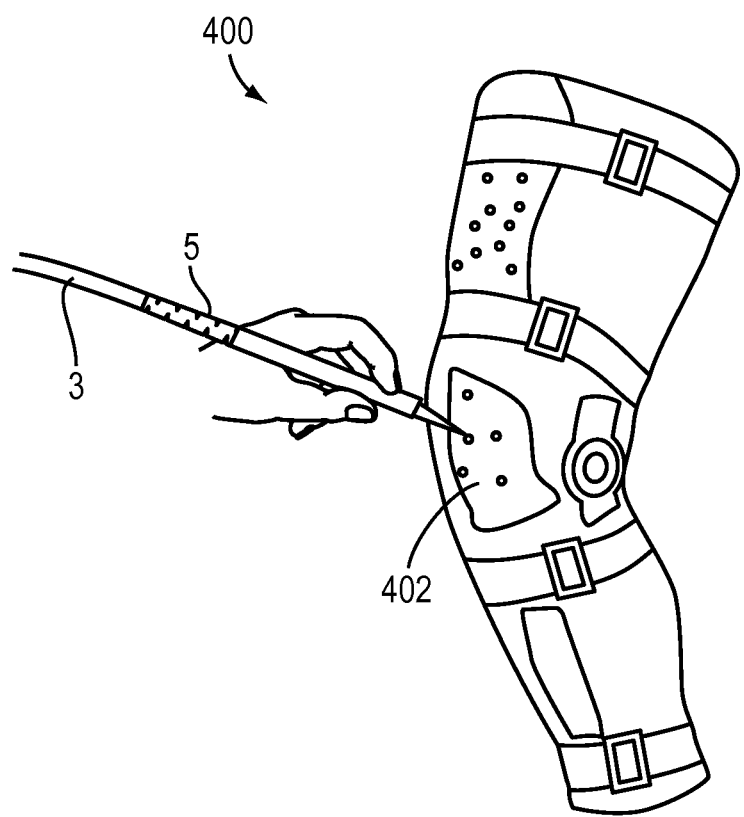
FIGS. 4A-4B are diagrams of scan delivery systems suitable for use with the device shown in FIG. 2.
Figure 4B:
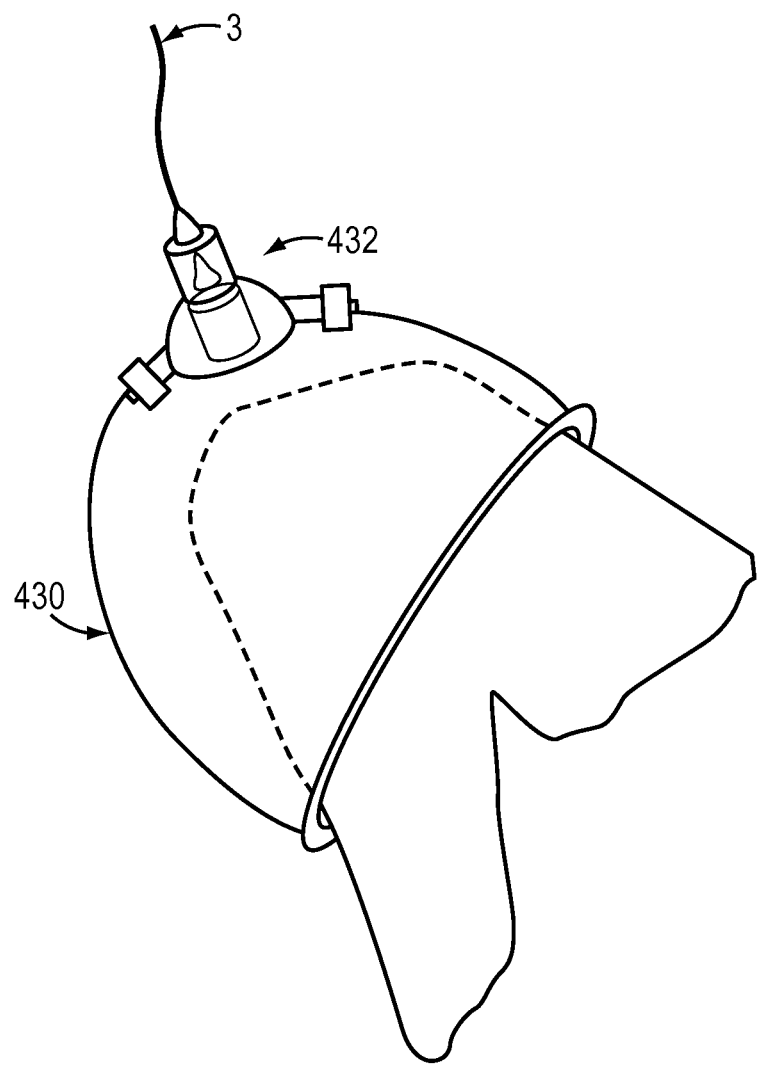

FIGS. 4A and 4B show different scan delivery systems for scanning a pulsed laser beam across the knee of a patient. FIG. 4A shows a bracing system 400 that includes ports 402 for treating predetermined target tissue on or within the knee with the hand unit 5 shown in FIG. 2. The ports 402 also insures that the beam is transmitted only to the targeted area. A patient may use this system 400 to treat himself without direct supervision by a clinician. The brace 400 may incorporate safety features that prevent the patient from accidentally emit signals that cause damage, such as a fail-safe that prevents the hand unit 5 from emitting a beam unless in the hand unit 5 is in contact with the skin.

FIG. 4B shows part of a computer-controlled system for automatic delivery of a pulsed laser beam with a laser transmitter 432. The system controls the location and dosage of the laser beam delivered to a region of the cartilage in the knee. The transmitter 432 can move laterally or up and down over the region of the knee through a transparent sphere surface 430, which can be made of plexiglass, plastic, or glass. The sphere 430 may be absorbing at the treatment wavelength (e.g., 1064 nm) to prevent accidental exposure to the treatment beam and transparent at the wavelength of the aiming beam (e.g., 633 nm) to facilitate treatment.

The sphere 430 is positioned over the knee and provides an indexing reference point for positioning the laser transmitter. Once the transmitter 432 is properly positioned on the sphere 430, and the sphere 430 is properly position on the knee, the system may be used to apply the proper dosage according to treatment parameters programmed by a clinician. The system may also be used for safe self-treatment by the patient. Both the scanning delivery system 400 and the computer-controlled system may eliminate or suppress beams that may be transmitted outside of targeted tissue.

Absorption Coefficient

Emission parameters may be selected such that the penetration depth of the laser beam is improved to reach locations arranged deeply within the body of a patient under treatment without damaging tissue passed by the laser beam or tissue surrounding the volume subject to the laser treatment. Deep penetration of laser radiation allows laser treatment of lesions, e.g., of cartilage tissue located at a relatively deep position within the body without damaging the surrounding biological tissue.

Light propagating through the biological tissue complies with Lambert-Beer's law such that its amplitude decays expo-nentially during passage through such tissue. The degree of penetration of the laser energy through the biological tissues depends on the coefficient of tissue absorption and on the fluence (energy per surface unit: $J/cm^2$) of the laser beam, i.e., the density of the beam energy. The fluence is given by the power density multiplied by the time of irradiation. The tissue absorption coefficient is a parameter that varies depending on the wavelength of the radiation. Therefore, the degree of penetration of the laser beam into a biological tissue directly depends upon the wavelength of the laser beam and upon the power of the laser beam: the higher the power of the beam the higher the degree of penetration into the tissue under treatment.

Figure 9:
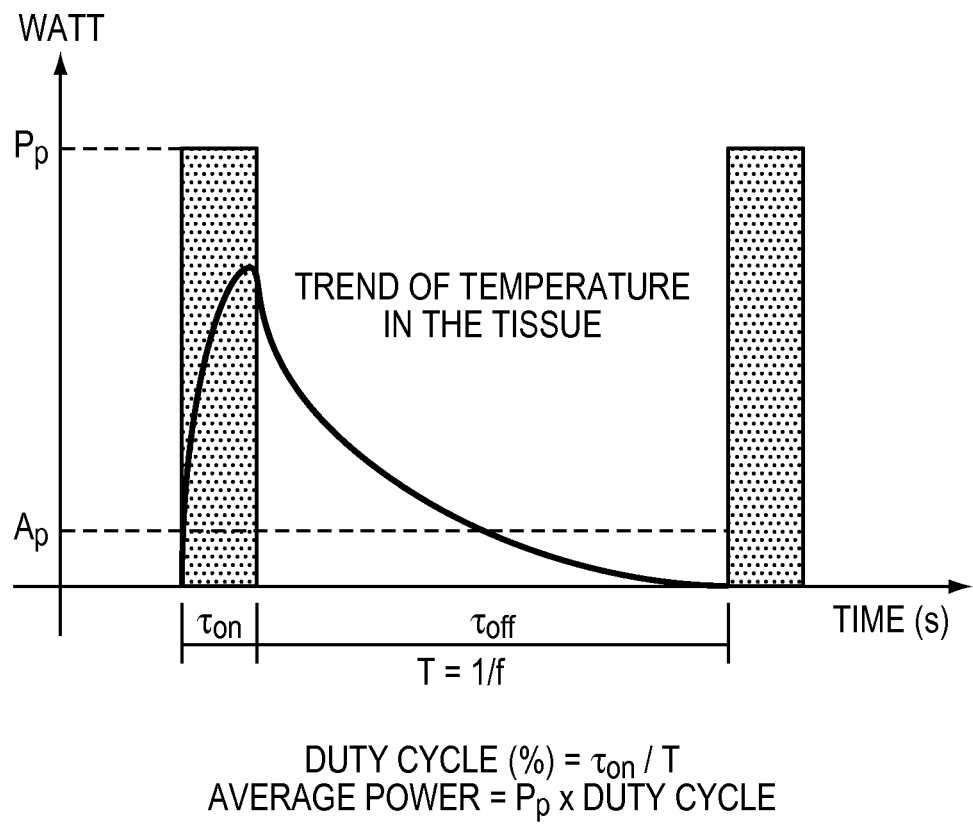
FIG. 9 is a diagram showing the tissue temperature trend during high intensity laser treatment according to the present invention.

Details on the effect of these parameters on the penetration depth of a laser beam in biological tissues are discussed in K. Dörschel et al., "Photoablation," SPIE, Vol. 1525 Future Trends in Biomedical Applications of Laser (1991), pp. 253-278. According to Dörschel et al. (1991) the optical penetration depth (x) of the light is inversely proportional to the index of tissue absorption ($\alpha$), i.e., $x=1/\alpha$. Therefore, the higher the tissue absorption coefficient ($\alpha$), the lower the penetration into the tissue. Dependency of the penetration depth on the above mentioned parameters is shown in FIG. 9 on page 261 of Dörschel et al. The higher the absorption coefficient, the poorer the penetration of the radiation through the tissue.

As shown in Table 1, the absorption coefficient ($\alpha$) for normal soft tissue is a function of wavelength ($\lambda$). A wavelength of 1,064 nm has the lowest absorption coefficient ($\alpha=4$ $cm^{-1}$) and the deepest penetration (2,500 µm). In contrast, the data reported by Dörschel et al. show that a $CO_2$ laser (wavelength 10,600 nm) has an absorption coefficient of 600 $cm^{-1}$ and a very low penetration depth.

TABLE 1

Regular absorption coefficient ($\alpha$) and effective absorption coefficient ($\alpha^*$□) (corrected for scattering) for normal soft tissue as a function of wavelength ($\lambda$)

| Wavelength | Absorption Coefficient | | Penetration Depth | |
|---|---|---|---|---|
| $\lambda$ [nm] | $\alpha$ [$cm^{-1}$] | $\alpha^*$ [$cm^{-1}$] | $1/\alpha$ [µm] | $1/\alpha^*$ [µm] |
| 193 | >400 | >5000 | <25 | <2 |
| 248 | 600 | 5000 | 17 | 2 |
| 308 | 200 | 1670 | 50 | 6 |
| 351 | 40 | 170 | 250 | 60 |
| 532 | 12 | 42 | 830 | 240 |
| 1064 | 4 | 5 | 2500 | 1900 |
| 1320 | 8 | | 1250 | |
| 2060 | 35 | | 286 | |
| 2700 | 1000 | | 10 | |
| 2940 | >2700 | | <4 | |
| 9600 | 700 | | 14 | |
| 10600 | 600 | | 17 | |

Data used herein for $\alpha$ comes from K. F. Palmer and D. Williams, "Optical properties of water in the near infrared," J. Opt. Soc. Am. 64, 1107-1110 (1974). Additional information on the penetration depth of different laser sources is presented in J. Tuner et al., Laser Therapy: Clinical Practice and Scientific Background, Prima Books, 2002, pages 40-43.

In order to achieve the greatest possible penetration, the laser light radiation is preferably minimally absorbed by the tissue chromophores, i.e., the wavelength of the laser light should not correspond to peak absorption wavelengths of the tissue chromophores. The most important chromophores include water, melanin, haemoglobin, oxyhaemoglobin and nucleic acids (DNA).

Figure 5:
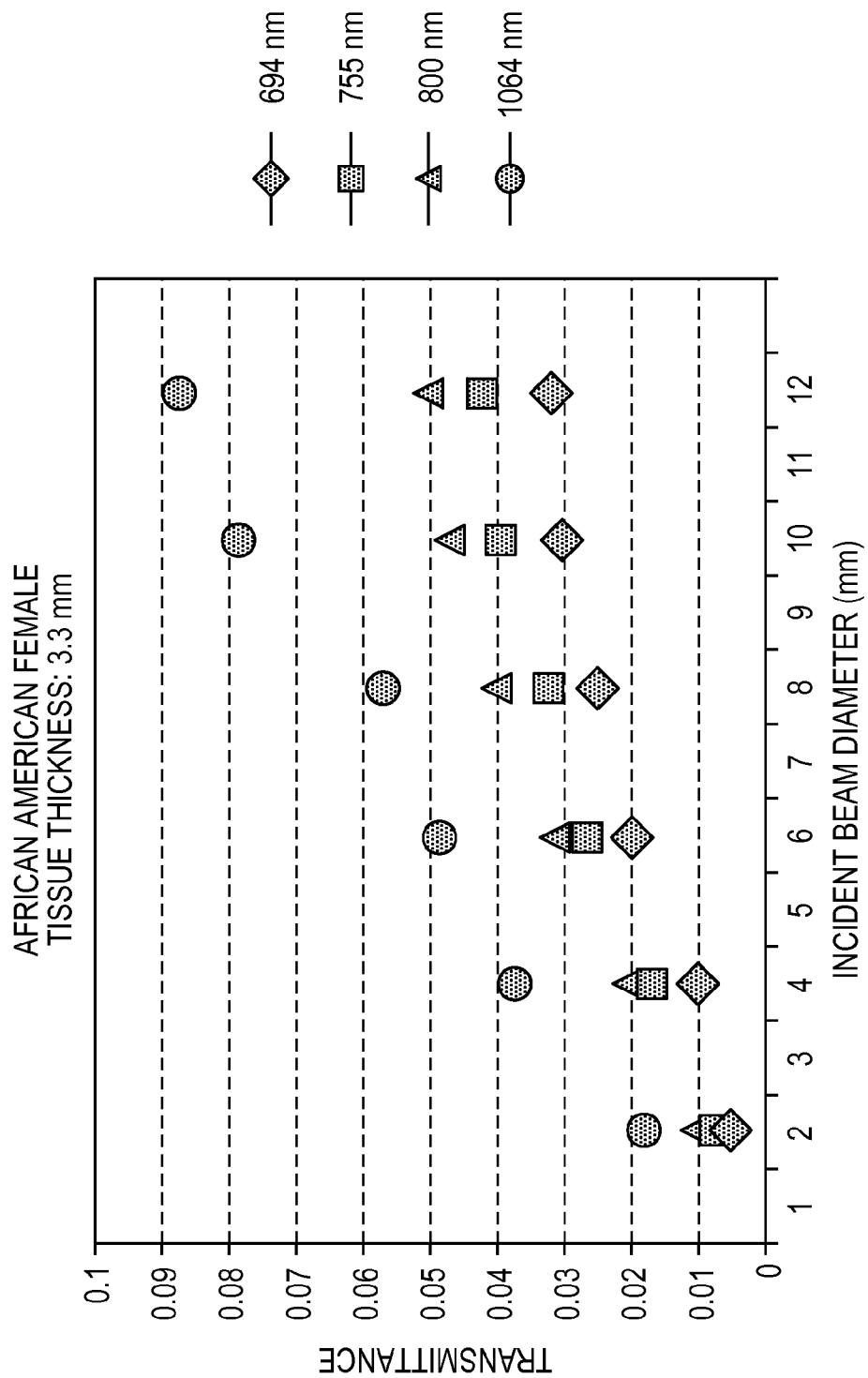
FIG. 5 is a diagram showing transmittance of four different wavelengths at six different spot sizes.

FIG. 5 is a plot of transmittance through 3.3 mm of hypermelanic tissue versus beam diameter for beams of visible and near-infrared wavelengths. Similar results hold for human skin with lighter colors, e.g., skin from European, African and Asian subjects, although the variation in transmittance is especially significant with darker skin, that is, subjects with hypermelanic skins (African skins). Generally, transmittance increases with beam diameter and, independently, with wavelength. Maximum transmittance occurs for beams at $\lambda=1064$ nm and beam diameters of 12 mm. This wavelength is only partially absorbed by the skin, melanin and subcutaneous fat and is able to go into deepest tissues (i.e., joint cartilage).

Therefore, according to one embodiment of the present invention, the pulsed laser beam has a wavelength between 0.75 and 2.5 micrometers. Alternatively, the pulsed laser beam has a wavelength between 0.9 and 1.2 micrometers. Alternatively, the pulsed laser beam has a wavelength of 1.064 micrometers.

Different wavelengths can be adopted, which are characterized by a low absorption coefficient. Therefore, according to another embodiment of the present invention, the pulsed laser beam has a wavelength with an absorption coefficient equal to or lower than 50 $cm^{-1}$ (absorption coefficient of water) in normal soft biological tissue. Alternatively, the pulsed laser beam has a wavelength with an absorption coefficient equal to or lower than 15 cm$^{-1}$ in normal soft biological tissue. According to still another embodiment of the present invention, the pulsed laser beam has a penetration depth of at least 2 mm.

Photomechanical Effect

One important aspect underlying the method of the present invention is that laser light, when used at a high intensity, may have a photomechanical effect at a therapeutic level on the tissues and/or cells being treated by the laser light. With a photomechanical effect, at least part of the energy of a laser light can be converted into one or more forms of mechanical forces on the tissues and/or cells being treated by the laser light. Such mechanical forces can have a physical effect on the cells and/or tissues being treated and cause the cells and/or tissues to change shape and/or size, resulting in such effects as stimulating cell metabolism, cellular proliferation, cellular differentiation, and then tissue regeneration.

According to a first aspect, by applying an appropriately defocused laser beam, having specific characteristics in particular in terms of Peak Intensity Fluence (PIF), at a given area of the tissue epidermis of a patient, the laser beam can have a photomechanical effect together with photothermal and photochemical effects on the tissues and/or cells being treated, in particular, those tissues and/or cells that are located deeply within the body of a patient under treatment, e.g., the cartilage tissue.

In spite of the high PIF used, the temperature increase at skin level must be kept to physiological range (37-41° C.) since too high a temperature increase would result in tissue damage. In order to achieve this result, according to the invention, a pulsed laser is preferably used.

In general terms, the interaction of an electromagnetic radiation with biological tissue depends upon the radiation wavelength and upon the optical properties of the tissue. A laser beam directed orthogonal to the surface of the tissue is partly reflected back due to the variation of impedance index when passing from the surrounding ambient (air) and the tissue. The remaining fraction of the laser beam energy is transmitted to and through the tissue and is absorbed and diffused several times by different chemical substances contained in the tissue.

Figure 6:
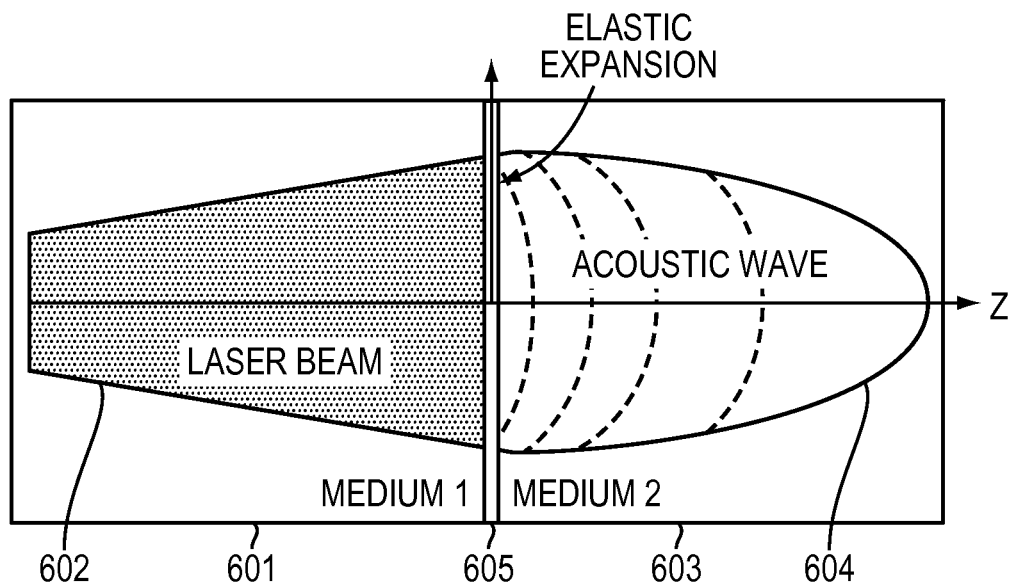
FIG. 6 is a diagram showing the conversion of an incident laser light into a photomechanical or photoacoustic wave at the interface between two media.

FIG. 6 is a schematic diagram that shows how a pulsed laser beam 602 generates an acoustic wave 604 a boundary 605 between a first medium 601 and a second medium 603. When the pulsed laser beam 602 impacts the second medium 603, an elastic pressure wave 604 is immediately created in the second medium 603 itself and propagates from the surface 605 deep down into the medium 603. The amplitude of the wave 604 is directly proportional to the intensity of the light beam 602 and inversely proportional to the pulse duration time. The wave amplitude also depends on the light properties (λ) and the physical-chemical structure of the second medium 603. Following is a formula describing the relationship between the sound wave shape created in the tissue hit by a high-intensity pulsed laser beam:

$$p_2(z, t) = \rho_2 v_2^2 \left( \frac{\alpha \sqrt{\hat{k}_1 \hat{k}_2}}{K_1 \sqrt{\hat{k}_2} + K_2 \sqrt{\hat{k}_1}} \frac{1}{v_2 + rv_1} \left( \beta_1 \sqrt{\hat{k}_1} + \beta_2 \sqrt{\hat{k}_2} \right) \right) I \left( t - \frac{z}{v_2} \right)$$

where the thermal diffusion coefficient is $\hat{k}_i = K_i/(\rho_i c_i)$; the dimensional coefficient is $r = (\rho_2 v_2^2)/(\rho_1 v_1^2)$; I is laser pulse intensity; $c_i$ is specific heat; $\beta_i$ is linear expansion coefficient; $K_i$ is thermal conductivity; $\rho_i$ is density; $v_i$ is sound speed; α is optical absorption coefficient of the tissue; z is depth; and t is time.

The relationships between incident laser light and the photomechanical or photoacoustic wave generated in the tissue include: (1) a direct relationship between the intensity of the incident light and the intensity of the mechanical wave created in the tissue; and (2) a direct relationship between the frequency of the mechanical wave and the pulse duration (τ) of the laser. That is, the shape of the acoustic wave is related to the shape of the laser pulse. The intensity of the mechanical wave may also depend on the optical, thermal, and mechanical features of the medium (e.g., medium 2 in FIG. 6).

Therapeutic Value of the Photomechanical Effect

High peak power values (e.g., those at least 1 kW) and high peak intensity values (e.g., those at least 1 kW/cm$^2$) allow a photomechanical effect to be exploited for therapeutic purposes. The "photoexpansion" and "photocontraction" effects mentioned above as examples of the photomechanical effects can substantially result in a sort of extracellular massage of the tissue subject to irradiation, when the peak power of the pulse, the pulse duty cycle and the pulse frequency are properly selected.

A non-limiting example of a photomechanical effect on the cartilage tissue is given in detail below, which gives one example of the therapeutic value of the photomechanical effect of a pulsed laser beam according to the present invention.

Hyaluronan (also called hyaluronic acid or hyaluronate; hereinafter "HA") is a non-sulfated glycosaminoglycan distributed widely throughout connective, epithelial, and neural tissues. It is one of the chief components of the extracellular matrix, contributes significantly to cell proliferation and migration. HA is an important component of articular cartilage, where it is present as a coat around each cell (chondrocyte). When aggrecan monomers bind to HA in the presence of link protein, large highly negatively-charged aggregates form. These aggregates imbibe water and are responsible for the resilience of cartilage (its resistance to compression). While it is abundant in extracellular matrices, HA also contributes to tissue hydrodynamics, movement and proliferation of cells, and participates in a number of cell surface receptor interactions, notably those including its primary receptor, CD44. HA is capable of binding volumes of water into a viscous, gelatin-like matrix. Besides providing compressibility to a tissue, proteoglycans also serve as reservoirs to growth factors into the ECM (e.g. bFGF). Any damage to the ECM then releases the bound growth factor, which can initiate the healing process. Proteoglycans can also be integral cell membrane proteins and in that capacity modulate cell growth and differentiation.

Figure 7:
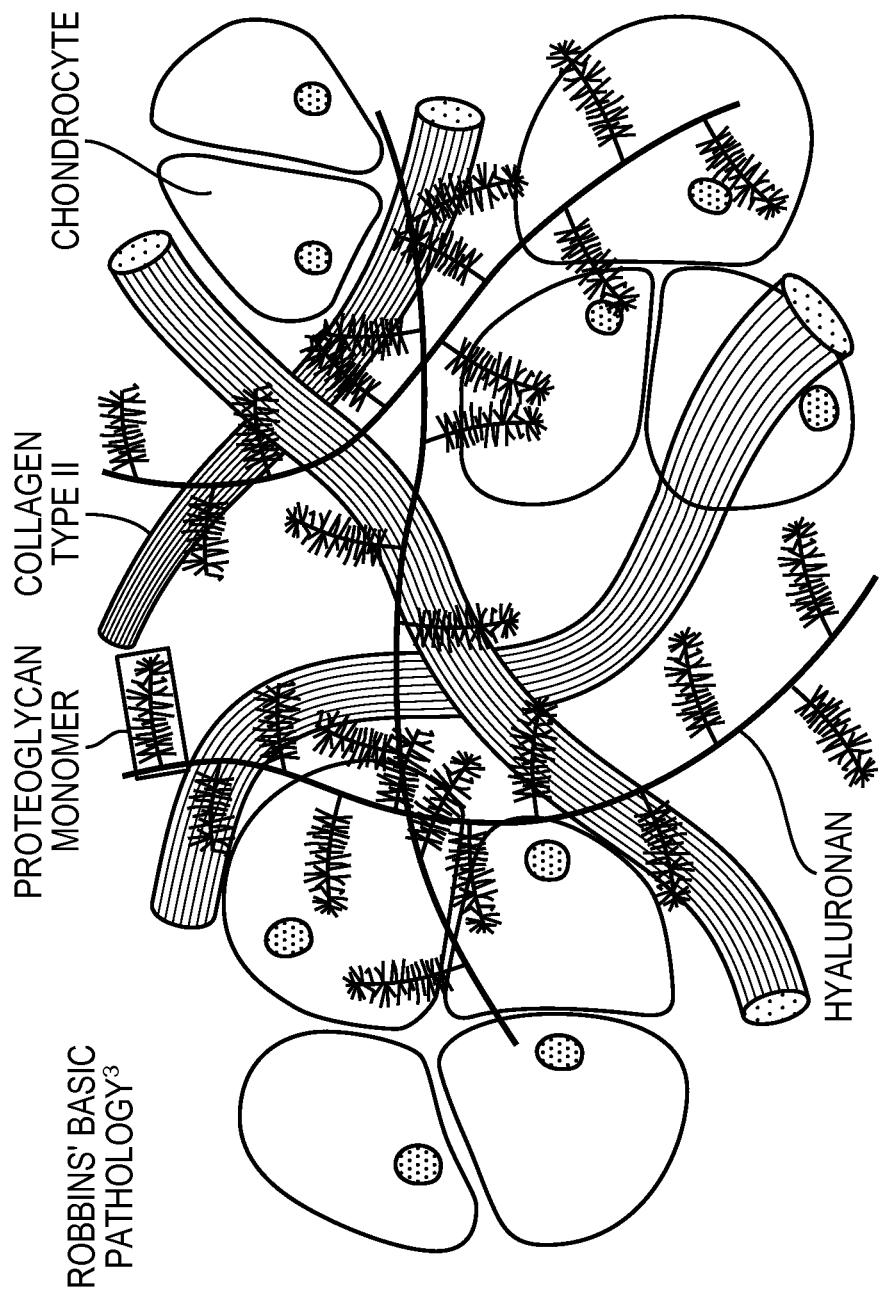
FIG. 7 is a schematic diagram showing the molecular structure of hyaline cartilage matrix.

FIG. 7 shows distribution of the HA in the extracellular cartilage matrix (ECM) as one of the most important components of the ECM. It is very important to point out that an intimate connection exists between the ECM and the chondrocytes. Any spatial deformation of the ECM is therefore automatically transferred to the cells as mechanical stimuli.

Figure 8:
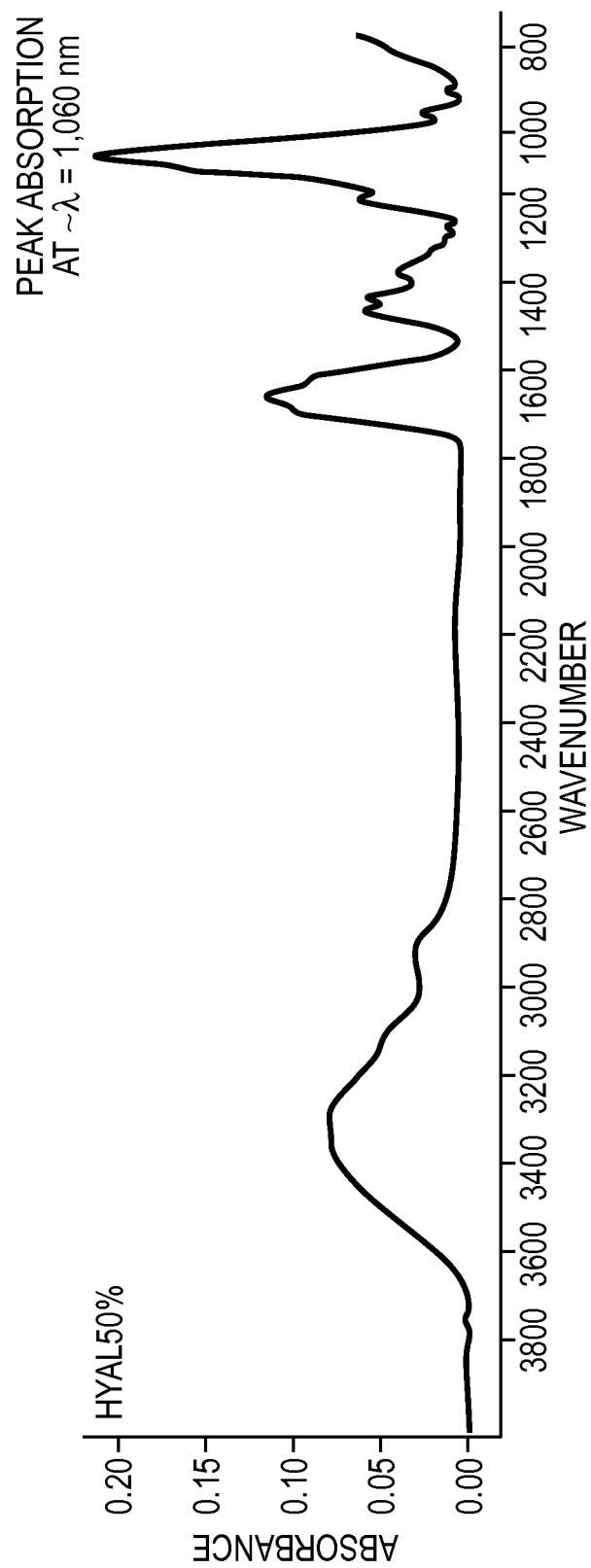
FIG. 8 is an absorbance spectrum of hyaluronic acid.

FIG. 8 shows the optical spectrum of HA. When a pulsed high intensity laser beam with an appropriate wavelength that falls within one of the absorption peaks of HA (e.g., a wavelength of 1064 nm) is used to treat a cartilage tissue, it is selectively absorbed by the HA content in the ECM. This specific absorption by the HA in the ECM via the pulsed emitting of this particular laser light is responsible for immediate tissue dilatation followed by contraction during the cooling phase. This reversible spatial deformation of the ECM is automatically transferred to the cells as mechanical stimuli.

The musculoskeletal system, which includes bones, cartilage, skeletal muscles and ligaments, responds to such mechanical stimulation with changes in metabolism, cytoskeletal organization, rate of proliferation, and state of differentiation during development (Onodera et al.). Chondrocytes also respond to mechanical forces by changing their metabolism, their state of differentiation, and their proliferation. They respond differently to mechanical force, depending on the magnitude, frequency, and mode of mechanical stimulation.

It is generally known that ECM adhesion through "Integrins" is important for cellular mobility, metabolism, and proliferation of different kinds of mesenchymal cells. Integrins are a family of transmembrane (α- and β-chain) heterodimeric glycoproteins whose intracellular domains associate with cytoskeletal elements. Integrins on epithelial or mesenchymal cells also bind to ECM; these interactions signal cell attachment and can affect cell locomotion, proliferation, or differentiation. Integrins-ECM interactions can utilize the same intracellular signalling pathways used by growth factor receptors; for example, integrin-mediated adhesion to fibronectin can trigger elements of the MAP kinase, phosphatidylinositol 3-kinase, and protein kinase C pathways. In this manner, extracellular mechanical forces can be coupled to intracellular synthetic and transcriptional pathways.

Differentiating chondrocytes express α5β1 and α2β1 integrins, and mature chondrocytes also express α5β1, α2β1, and αvβ5 integrins Inhibition of integrin-mediated cell-ECM adhesion enhances the chondrogenic differentiation of embryonic mesenchymal cells in a pellet culture system. Generally, cell-ECM adhesion through integrins activates small GTPases and the mitogen-activated tyrosine kinase (MAPK) pathway and alters cytoskeletal structures. Simultaneously, downstream signalling of integrins through these pathways could be a potent mechano-transduction pathway in chondrocytes. Indeed, different kinds of mechanical loadings activate the extracellular-regulated kinase pathway (ERK-1/2) in chondrocytes, which is the dynamic component of loading on cartilage explants rather than free swelling. Takahashi et al. indicated that an expansive force induced phosphorylation and nuclear translocation of ERK-1/2 in vivo. Therefore, cell-ECM adhesion could play a crucial role in mechano-transduction and the subsequent responses of chondrocytes to mechanical stimulation.

Cell growth and differentiation involve at least two different types of signals acting in concert. One derives from soluble molecules such as polypeptide growth factors and growth inhibitors. The other involves insoluble elements of the ECM interacting with cellular integrins.

Since cells are virtually transparent to the high intensity laser light wavelengths according to the present invention (e.g., 1064 nm), which is able to reach the deepest tissues such as articular cartilage, the high intensity laser light according to the present invention can convert laser light, selectively absorbed by HA, into mechanical forces, which, by acting on ECM, are able to mechanically stimulate chondrocytes.

Photothermal Effect

As stated above, the tissue penetration is proportional to the power used, and consequently, the intensity (W/cm$^2$) or power density and consequently to the Peak Intensity Fluence. In order to reach deep tissues, high power values have to be adopted, at the same time avoiding tissue damages caused by, e.g., photothermal phenomena.

Power laser systems supply high quantities of energy even in short periods of time, which inevitably leads to heating of the area being treated. The heat generated in the tissues is directed correlated to the quantity of energy transferred to the same.

In continuously emitting laser systems, an increase in the emission power results in an increased emitted energy, which is the integral of the power in time. Part of said energy is transformed into heat in the irradiated tissues. The speed of propagation of the heat in water (the biological tissues being mainly formed by water) is much lower than the speed of propagation of the electromagnetic radiation in the tissue. As a consequence, the heat generated by the laser energy in the tissues accumulates at a certain depth under the skin of the patient being treated with consequent negative effects due to temperature increase.

The diffusion length of the heat in a biological tissue is an important parameter for controlling the thermal effects during laser treatment. Such length L is given by $$L^2 = 4Kt$$

where K is called thermal diffusivity of the material where the heat is propagated, and is a function of the thermal conductivity, specific heat and density of the material; and t is time.

From the above formula, given that for water K=1.43× 10$^{-3}$, heat energy propagates in water at 0.8 mm per second. By putting the diffusion length L equal to the penetration depth of a laser radiation, the relaxation time is obtained as follows $$t_{relax} = \tfrac{1}{4} K x^2$$

where $t_{relax}$ is the relaxation time, K is the thermal diffusion coefficient of the tissue and x is the penetration depth.

For a Nd:YAG laser with a penetration depth equal to ¼ cm, and assuming for K the value 0.00143 (the value of water), the relaxation time is 312.5 seconds. This means that if a Nd:YAG laser is used to reach deep penetration into the tissue, a rather high thermal relaxation time is obtained. This causes a slow temperature increase in the tissue under treatment and a slow thermal dissipation. Such a slow dissipation might lead to heat accumulation and consequent damages in the tissues under treatment.

As mentioned above, in order to treat tissues located deeply in the body, a wavelength characterized by a low water absorption coefficient is preferably used (the lower the tissue absorption coefficient of light radiation, the greater its tissue penetration). While this enables one to transport the light deep into the body, e.g., inside the joint cavities, it also creates a potential problem regarding the heat dissipation speed generated in the irradiated tissue (the greater the propagation speed of the light in the tissues, the greater the risk that the heat induced remains "trapped" deep down, giving rise to thermal accumulation phenomena). Therefore, to avoid thermal accumulation and excessive temperature increase in the tissue under treatment, it may be necessary to provide sufficient time between successive laser pulses, for the heat to dissipate.

In essence, the laser light is at least partially converted into a thermal wave, which is responsible for the photoexpansion effect observed with outright temperature increases of up to 42° C. During τ-off time, there is a rapid cooling and the medium (e.g., the tissues) moves towards a photocontraction effect. Photoexpansion and photocontraction can be the expansion and contraction, respectively, of a medium, due to the generation and dissipation, respectively, of heat converted from a laser light. As the tissues do not undergo any drastic deformation, the expansions and contractions are reversible. This photomechanical behaviour, which is capable of generating an acoustic wave and is therefore also known as the photoacoustic effect, is in all probability the origin of a wide variety of curious photomotions observed in these systems, including micron-scale surface mass transport.

An additional important parameter having an influence on thermal accumulation and therefore on the temperature increase is the overall volume of tissue under treatment. Keeping the irradiated surface (i.e., the laser spot) and the irradiated energy constant, an increase of the peak power per pulse increases the irradiated volume. The reason for this is that a higher peak power provokes a deeper penetration of the laser in the tissue, and therefore an increase in the overall volume absorbing the laser energy. The penetration depth is understood as the depth at which the density level of the laser radiation is capable of exerting a therapeutic effect.

In an isoenergetic thermodynamic transformation, different thermal capacities ($C_k$) correspond to different volumes, in accordance with the following equation:

$$C_k = c_k \times m$$

wherein: m=body mass; and $c_k$=specific heat, typical of each body.

Because $C_k = \Delta Q/\Delta T$, wherein Q=energy; and T=temperature, we have:

$$c_k \times m = \Delta Q/\Delta T$$

Therefore, $\Delta T = \Delta Q/(c_k \times m)$.

It is evident from the equation above that, the same amount of irradiated energy causes a temperature increase which is inversely proportional to the irradiated volume: the larger the irradiated volume the smaller the temperature increase. Therefore, and contrary to what might appear at first glance, an increase of the peak power of each laser pulse improves the conditions of treatment from the point of view of tissue temperature control.

It has been therefore recognized that in order to obtain an effective treatment of the deep tissues without damaging more superficial and surrounding tissues, a pulsed laser source with low pulse frequency and short pulses (i.e., low duty cycle values: short τ-on times and long τ-off times) is preferably used, in combination with high peak power values per pulse.

The area of the laser spot is also very important in order to maximize the greatest possible penetration, while minimizing the amount of scatter. It has been demonstrated in experiments (Zhao, 1998) that by increasing the diameter of the spot size there is a reduction in the scattering angle (the larger the diameter of the spot, the lower the scattering angle). This results in a deeper penetration, more uniform diffusion of the radiation in the tissue, and therefore an increased therapeutic effect.

In addition, because $\Delta T = \Delta Q/(c_k \times m)$, as shown above, with the same energy per pulse, the greater the volume treated, the lower the thermal increase to the tissues. One way to increase the volume treated, especially when the penetration depth is preferably kept at a constant value, is to increase the spot size. By properly selecting the above discussed parameters, the tissue temperature in the treated volume is kept below a certain temperature, e.g., 42° C. or even lower, and preferably below 40° C. If required, cooling of the skin of the patient under treatment can be additionally provided.

Photochemical Effect

The pulsed high intensity laser beam according to the present invention can also have a photochemical effect on the tissues and/or cells being treated. With a photochemical effect, at least part of the energy in a laser light can be directly taken up by the tissues and/or cells being treated by the laser light. The direct uptake of the energy in a laser light can have certain chemical and biochemical consequences in the tissues and/or cells being treated. The energy directly taken up by the tissues and/or cells being treated with the laser light is not converted to a mechanical force as in the photomechanical effect.

One non-limiting example of photochemical effects of a laser light is to provide kinetic energy for enzymes to get over the energy threshold to start a biochemical reaction. This example is elaborated in detail below.

In order to fully understand and describe the way of action of the laser radiation on an injured biological tissue, it is crucial to consider the clinical phenomena observed during the laser therapy. At least four different levels of investigation shall be considered: clinical, biochemical, molecular biology-related, and physical.

As a matter of fact, by putting physical considerations before the biochemical aspects, it is not possible, for example, to reconcile the clinical efficacy of the radiation at 10,600 nm ($CO_2$ laser) with its optical properties related to biological tissues. That being stated, it is therefore crucial to first consider the therapeutic effects of the laser, as reported in the literature of the last twenty years: i.e., the anti-inflammatory, biostimulating, antalgic, antiedemic and lipolytic effects.

In the animal model of osteoarthritis pathology it has been found that the application of the method according to the invention causes a drop of PCR (reactive protein-C) values. This is due to a reduction of the incretion of cytokines such as IL-6, IL-1β and TNFα. Incretion is a glandular secretion which is intended to remain and act inside its generating organism.

The cytokines reduction is not due so much to a direct effect of the laser action over these or other phlogogenic cytokines, as to the stimulation induced by the laser on certain grow factors, such as TGFβ and IGF-I, which have an antagonizing effect over said cytokines Cytokines are proteinic, hormone-like factors produced by a wide range of cells. They exert a number of different biological effects, among which the control of the inflammatory, grow and cellular differentiation processes, as well as of the immunological responses processes of a host, by acting as intracellular messengers. The best known cytokines are the tumoral necrosis factor (TNF), the interferons and cytokines. Also known are cytokines of phlogogenous type which activate catabolic processes leading to tissues destruction, and anabolic cytokines which, on the contrary, promote the regenerative processes.

Accordingly, the laser radiation does not provide any blocking action on any cellular structure or product (for example, IL-β, TNFα, IL-6), but can promote, with a readily available energy, the anabolic cytokines able to reverse the catabolic process under way.

This stimulation actually takes place by acting both on the cellular receptors, having an intrinsic tyrosinchinasic activity, and on those which utilize receptors associated to intracytoplasmic tyrosinchinase.

Belonging to the former type is a group of receptors having the insulin as prototype. In particular, the group includes the receptor for the insulin-like-growth factor (IGF-I), the receptor for the Transforming Grow Factor beta (TGFβ), the receptor for Epidermic Grow Factor (EGF) and that for Platelet-Derived Grow Factor (PDGF). Following the activation by interaction between the receptor and the hormone, it is possible to modulate the activity of other molecules involved in the cellular proliferation.

In other words, these receptors have such a structure as to be able to directly change the cellular activity, once they have been activated by the specific hormone (e.g. IGF-I).

The receptors of the second group, which utilize intracytoplasmic tyrosinchinase, are also called receptors of "GH/cytokines," since to this group belong the receptors of GH, prolactin, erythropoietin and of a number of cytokines.

The laser favors, in the first place, the tyrosinchinasic activity of the receptors having intrinsic activity (thus increasing the IGF-I, TGFβ, EGF, PDGF factors) and secondly those having intracytoplasmic tyrosinchinase (by improving the GH effect).

To understand the operating mechanism generated by the laser it is worth remembering how the enzymatic systems work. These operate in a way similar to the inorganic catalysts, but have a much higher specificity of action. In fact, the enzyme adsorbs selectively the sublayer on which it acts and becomes intimately joined therewith.

Once they have reacted, the molecules adsorbed by the enzyme are less strongly bonded and move away from the enzyme which becomes available again. It should be born in mind that the major object of an enzyme (similarly to a catalyst) is to reduce the triggering (kinetic) energy necessary for the molecules to enter a given reaction cycle. The catalyst and the enzyme, therefore, reduce the energy requirements, that is, the energy threshold the molecule has to get over to start the reaction.

Under stress conditions, such as those induced by chronic infections, an increase in the phlogogenous cytokines takes place, which brings about the activation of intracytoplasmic tyrosinchinase receptors with a competitive interference over the GH. This phenomenon could provide an explanation of the reason why the anabolic phenomena of the cell are not completely blocked, but are in fact prevented because of a phenomenon of enzymatic and energetic competition.

In this situation, the readily available energy from the laser favors the pathway of intrinsic tyrosinchinase receptors, not that of the intracytoplasmic ones (already engaged by the phlogogenous cytokines), with a preference for such grow factors as the (IGF-I), Transforming Grow Factor β (TGFβ), Epidemic Grow Factor (EGF) and Platelet-Derived-Grow Factor (PDGF), which tip the homeostatic cellular scales in favor of the anabolic pathway instead of the catabolic one.

At this level, the laser operates in two distinct ways:

directly on chemical reagents: this is probably the first pathway of intervention; in fact, during a chronic and/or degenerative inflammation, a saturation of the cytoplasmic tyrosinchinase takes place due to the stimulation of the "GH/cytokines" induced by the phlogogenous cytokines (IL-β, TNFα, IL-6 etc.) which largely prevail over the anabolic cytokines (GH, IGF-I, TGF, etc.). Under this condition, the availability of kinetic energy delivered by the laser radiation would favor the direct access of the cellular reagents to the cycle of metabolic reactions, induced by the anabolic cytokines, also in case of a shortage of tyrosinchinase enzyme (shortage due to the action of the phlogogenous cytokins). As a rule, with no enzyme action, it is not possible to activate the anabolic reactions, as the required energy is too high: the laser does provide for such energy. In this mode, the cell would have the possibility of starting again the anabolic activities interrupted by the inflammatory condition. The essential difference between the laser and the medicines having anti-inflammatory activity lies in the fact that the laser stimulates the anabolic cytokines towards resuming their metabolic efficacy and does not block any activity, contrary to anti-inflammatory drugs which inhibit some metabolic pathways (including those of the phlogogenous cytokines) without promoting anything. It is interesting to note how the blockage of the TNFα determines only a slowing down of the degenerative phenomenon under way, but not a reversal of tendency, contrary to what can be observed in vivo when using laser radiation. The absence of reversal of tendency, in spite of the blockage of TNFα, can be explained by considering that the other phlogogenous cytokines go on with their antagonist activity by binding the tyrosinchinase;

indirectly on the tyrosinchinase (membrane, cytoplasm): in this case the laser makes greater amounts of tyrosinchinase available by activating its enzymatic precursors. Such higher quantity of intracytoplasmic tyrosinchinase allows the occurrence of metabolic activities induced by the paracrine role of GH (anabolic cytokine).

In conclusion, the laser radiation at the power intensity levels disclosed above leads at first to an initial by-pass effect by promoting the metabolic activities of the grow factors. Afterwards, it makes greater quantities of intracytoplasmic tyrosinchinase available, which are useful to the pathway of GH.

It is known that the TGFβ has, at high doses, an antagonist effect versus the TNFα, the latter having a significant role in the genesis of osteoarthritis phenomenon. Also known is the fact that IL-1β and TNFα an increase the availability of receptors for glicocorticoids. All of these, in the case of inflammation cronicity, contribute to orienting the organism towards the catabolic pathway rather than the anabolic one, thereby increasing the degenerative phenomena. Lopez Calderon et al. (see Lopez Calderon A, Soto L., Martin A I. Chronic inflammation inhibits GH secretion and alters serum insulin-like-growth factor system. Life Science. 1999:65(20):2049-60) have reported the results of in vivo experiments describing that the chronic inflammation inhibits the secretion of GH and alters the serum levels of IGF-I.

A whole string of positive effects due to the axis GH-IGF-I in the homeostatic scales of the organism is known, said axis being modified when a cachexic or degenerative phenomenon takes place.

The laser radiation, when delivered with an intensity sufficient to pass the activation threshold, is able to promote the cellular activities without inducing any "pharmacological blockage" of any type. It is known, in fact, that a significant limit of the anti-inflammatory drugs lies in the fact that, by acting with a blocking effect on some biological functions, they always cause undesired side effects (the TNFα, for example, induce a serious weakening of the immune system).

In short, the laser, by supplying readily available kinetic energy, favors in the first place the activation of the receptor pathway for intrinsic tyrosinchinasic activities, notwithstanding any enzymatic deficiency. This promotion triggers a series of intracellular and extracellular phenomena which affect, by improving them, the grow factors IGF-I, TGF, EGF, PDGF. In the second place the activation of the intracytoplasmic tyrosinchinase takes place, which boosts the effect of GH by restoring the axis GH/IGF-I, and of the cytokines.

This explains why, under particular conditions, the laser has no anti-inflammatory effect, but does have a prophlogistic effect which improves and sustains the immune system.

Another non-limiting example of photochemical effects of a laser light is the activation of molecular messengers (e.g., $Ca^{2+}$ channels and its cellular downstream messengers). This example is elaborated in detail below.

It is well known that cells strictly manage cytoplasmatic $Ca^{2+}$ level. Physiological intracellular $Ca^{2+}$ concentration is 20,000 times lower than extracellular $Ca^{2+}$ concentration. Since there exists a trans-membrane electrical gradient (−60, −90 mV), $Ca^{2+}$ tends to spontaneously enter the cells. Cell membrane is partially porous to ions $Ca^{2+}$ and there exists the problem to keep the intracellular $Ca^{2+}$ concentration low to avoid cellular death. Therefore, in order to avoid that toxic intracellular $Ca^{2+}$ concentrations, cells assume an oscillatory behavior, capable of controlling the intracellular $Ca^{2+}$ concentration. This mechanism provokes intracellular propagation of $Ca^{2+}$ waves called "chemical waves." These chemical waves are sensitive to electromagnetic field oscillations in which cells are dipped. Therefore, these chemical waves are also sensitive to laser energy delivered by a pulsed laser beam. By affecting the chemical waves, a pulsed laser beam can have an effect on the intracellular $Ca^{2+}$ concentration, and thus can have a series of biochemical and biological consequences.

Comparison of the Photomechanical and Photochemical Effects

While all laser systems can deliver the energy needed to have a photochemical effect on the tissues and/or cells being treated, only high intensity lasers can exert a photomechanical effects of therapeutic value. High peak power values (e.g., those at least 1 kW) and high peak intensity values (e.g., those at least 1 kW/cm$^2$) allow a pulsed laser light to have both a photomechanical effect and a photochemical effect on the tissues and/or cells being treated, which, in combination, can achieve extraordinary and unexpected therapeutic results.

According to an embodiment of the invention, tissue regeneration is enhanced by exploiting said photomechanical effect induced by the high powered-pulsed laser beam on the tissue being treated, in combination with a direct photochemical effect induced by the laser photons on the cells. Cartilage tissue is characterized by an extra-cellular matrix, wherein the tissue cells are contained. The photomechanical effect induced by the pulsed high intensity laser causes repeated contraction and expansion of the extra-cellular matrix and of the cells contained therein. This mechanical effect stimulates a chondrogenic action. The direct photochemical effect, i.e., direct absorption of energy from the laser photons by the cellular structure, controls the cell differentiation such that healthy hyaline cartilage tissue is regenerated rather than fibrous cartilage tissue.

The relationship between dose of laser radiation and efficiency of the treatment has always been considered important for the therapeutic action of the laser. This fact has been widely reported in the literature, based on in vitro experiments.

In vivo experiments conducted on knee joint in rats, have shown that a power density of 5.8 W/cm$^2$ may not be sufficient to pass the activation threshold. (Usuba M, Akai M, Shirasaki Y: Effect of low level laser therapy (LLLT) on viscoelasticity of the contracted knee joint: comparison with whirlpool treatment in rats, Laser Surg Med 1998, vol. 22 pp. 81-5).

The present invention is based on the surprising recognition of the importance of the intensity of the laser radiation on tissue rather than the "dose" thereof, i.e., the total energy applied during the whole treatment. Because LLLT can only have a photochemical effect, and sometimes also a photothermal effect, it is conceptually different from the high intensity laser therapy (HILT) according to the present invention, which has a photomechanical effect as well as a photochemical effect as well as a photothermal effect. The photomechanical effect according to the present invention also relates to photothermal effect and photoacoustic effect as detailed above.

It is necessary make a clarification here: one thing is the photothermic effect of any energy source which, when applied to a tissue, raises the average temperature and therefore, also the basal metabolism. This phenomenon can also easily be obtained with a simple low power laser with continuous emission on a body area for a long time. Instead, the thermal effect correlated with the photodynamic effect is very different. In this case it will be necessary to have a pulsed laser with very energetic and very short pulses, in other words, a HILT laser. The irradiated tissue dilates rapidly due to the thermal effect and then cools down immediately afterwards, between one pulse and the next. Also in this case, the thermal effect is immediately transformed into mechanical energy.

This is why we talk about the relationship between the photothermal effect and the photomechanical effect. But this is only a very particular case! The same laser can therefore have two thermal effects, one immediate with photoexpansion followed by contraction during the cooling, and the other more general due to a phenomenon of thermal accumulation that determines an increase in the average temperature of the area being treated, with the consequent raising of the basal metabolism. The first phenomenon is only typical of the HILT while the second is common to all the energy sources applied to a body.

Distinctions between HILT and LLLT

In view of the above, HILT distinguishes over LLLT in respect of the purposes to be achieved and selection of operating conditions and parameters to achieve said purposes and objectives. As far as the purposes are concerned, the main object of the HILT is the non invasive regenerative therapy with a non-painful and non-invasive therapeutic system. Secondary objectives of the HILT is treatment of deep lesions, such as lesions of the articular cartilage.

This can be obtained thanks to HILT's photomechanical effects in addition to and in combination with photochemical and photothermal effects, thanks to the high peak power values adopted; transfer of high-energy photons at the deepest level possible within the tissues; and control of tissue temperature below 42° C., and preferably below 40° C.

The above objectives are achieved by following some general rules: the deeper the penetration of the laser radiation, the longer the time between subsequent laser pulses, to allow for thermal dissipation; the higher the energy content per laser pulse, the lower the pulse frequency, i.e., the frequency at which the laser pulses are repeated; the higher the power level per pulse, the lower the fluence; the higher the peak power of each pulse, the shorter shall be the pulse duration (low duty cycle); the higher the peak power, at constant spot area, the larger will be the volume interested by the radiation and therefore the lower will be the increase in temperature due to heat accumulation; the higher the energy per pulse, the shorter will be the total exposure time to the laser radiation; and the shorter the total exposure time to the laser radiation, the lower will be the heat accumulation.

Big pulses, characterized by high peak power and a high amount of energy per pulse, are useful for transferring in depth high amount of energy in accordance with Lambert Beer's law. Thermal increase of tissue temperature is directly correlated to the amount of energy supplied. In order to obtain the correct control of the temperature trend while achieving the photomechanical effect during treatment, the following values can be indicated as an example of the method for stimulating tissue regeneration (it should be noted that various parameters of the laser emission may vary within the ranges mentioned throughout the application):

the highest possible peak powers (e.g., at least 1 kW);

very long delivery time T (e.g., between 0.1 and 1 second) characterized by a very short pulse duration $\tau$ (e.g., between 1 and 300 microseconds); therefore, very low repetition frequency of the pulses (e.g., between 1 and 40 Hz) and very low duty cycle (e.g., at most 0.01%).

a high energy content per pulse (e.g., between 0.03 and 1 Joule) capable of guaranteeing very high pulses and a good average power (e.g., tens of W) that guarantees a good transmission of photons to the target despite any scattering that the light undergoes during its passage;

a large laser spot diameter (e.g., 10 mm); and a PIF between 0.1 and 1.0 $(J/cm^3)^2$.

High energy delivered in this way is safe and allows for a sudden dramatic dilation of the volume throughout the tissue when the light is on, followed by a cooling beat when the light is off, thereby creating a photomechanical effect.

Evaluation Studies

Experimental trials carried out with HILT in vitro and, in vivo on both animal and human models enabled us to draw a map of the Peak Intensity Fluence (PIF).

| | |
|---|---|
| LLLT | 0.00146 |
| HILT | |
| Anti-inflammatory effect (vivo) | 0.045 |
| Chondrocytes (vitro) | 0.246 |
| HCT8 (vitro) | 0.776 |
| Chicken study (vivo) | 0.553 |
| Humans (vivo) | 0.553 |
| First sheep study (vivo) | 0.566 |
| Horse/Sheep new study | 0.879 |
| Toxic dose, chicken study (vivo) | 1.688 |

High Intensity Laser Therapy (HILT) stimulates cells proliferation in vitro.

Background and Objectives:

Nd:YAG laser emissions are widely used in physiotherapy and sport medicine for pain management but little is known about their effect on cell proliferation. Lower power diodic laser emissions show a cytoproliferative effect, but they can't be safely or effectively used to treat deep degenerative disorders. Recently a new kind of Nd:YAG laser emission (HILT, High Intensity Laser Therapy) has been devised, whose features makes it possible to safely deliver high amounts of energy to deep seated anatomical locations. This in principle could allow for the treatment of degenerative disorders, like osteoarthritis. The objective of this study was therefore to assess if a) HILT has a cytoproliferative effect, b) for which emission parameters this effect can be observed, and, if the effect can be observed, c) to determine if it is due to an interaction with the tyrosine kinase signalling pathway.

Materials and Methods:

In vitro cultured HCT8 cells were irradiated with the HILT emission, at different emission parameters, and their proliferation rate was determined through an OD assay and immunohistochemical tests determining the levels of the most common nuclear cell cycle activation markers (Ki67, PCNA, Cyclin D1), and of growth factors (IGF I) synthesis. The same experiment was repeated on HCT8 cells treated with genistein, a selective inhibitor of the tyrosine kinase pathway leading to the cell cycle activation.

The laser system used in the study has a wavelength of 1064 nm, a pulse duration of 200 microseconds, an energy per pulse between 0.30 and 150 mJ, a repetition frequency between 1 and 40 Hz, a spot size diameter of 6 mm. The power supply for the laser system is 230V-50/60 Hz. The input is 12 A.

The laser settings per treatment are as follows:
Peak Intensity Fluence (PIF): 0.776
Peak intensity: 2.7 kW/cm$^2$;
Energy per pulse: 150 mJoule;
Repetition frequency: 10 Hz;
Spot size diameter: 5 mm;
Fluence per pulse: 0.759 J/cm$^2$;
Energy per treatment (dose): 27-36 J;

Results:

HILT emission was capable of inducing cell proliferation at given emission parameters. While the total amount of energy and the dose delivered did not correlate with the proliferation rate, the frequency of repetition of HILT pulses, the exposure time and the average power played a crucial role. Moreover, HILT treatment was capable of restoring the expression of the cell cycle markers inhibited selectively by genistein.

Conclusions:

HILT is capable of restoring the activation of the cell cycle, at given emission parameters, and of stimulating cell proliferation. The mechanism of activation could rely on a direct interaction with the tyrosin kinase signaling pathway, or on the induction of alternative pathways, perhaps mediated by a photomechanical cell stimulation. At the active parameters, HILT stimulates the autocrine and paracrine activation of proliferation mediated by the IGF I growth factor.

Hyaline Cartilage Regeneration in vivo Animal Model Using HILT

Introduction:

The aim of the research conducted in this example is to assess HILT as a new non-invasive method to stimulate articular cartilage re-growth in vivo using an animal model. The primary goals were to assess the safety and effectiveness of HILT in vivo. Other goals included the assessment of re-growth of the cartilage and anti-inflammatory effect of HILT.

Materials and Methods:

Sheep was chosen as an animal model in this study because sheep, among all animal species tested, had a basal metabolic rate (BMR) among those closest to humans (R. K. Porter, "Allometry of mammalian cellular oxygen consumption. CMLS, Cell. Mol. Life Science. 58 (2001): 815-822).

The femoral trochlear sulcus of the patella was chosen as the site of the lesion. This site is partially covered by the patella and light has to pass through the space between the patella and the femur. The average distance between the skin and the center of the lesion is 22±1.7 mm (medial) and 30±1.5 mm (lateral). In order to calculate the intensity of light inside the tissue, a photodiode was inserted into the bone of the femoral trochlear sulcus of the patella (dead sheep's knee) at the same site as the lesion. A data logger was used to track heat, light and power. The data logger is equipped (photodiodes, optical fibers, etc.) with small sensors that allow measurement in difficult conditions At time zero (T0) monolateral cartilage full thickness surgical defects reaching the subchondral bone was created in ten female adult sheep, weighing 60±5 kg, by drilling (Ø=14 mm) of the femoral trochlear sulcus of patella.

All subjects (n=10) received antibiotics prophylaxis for 6 days postoperatively.

One week later surgery all subjects were divided into two groups: the HILT group received 15 treatments (Tx) of laser while untreated group didn't received laser.

The laser system used in the study has a wavelength of 1,064 nm, a pulse duration between 50 and 110 microseconds, an energy per pulse between 200 and 2000 mJ, a repetition frequency between 1 and 10 Hz, a spot size diameter of 10 mm. The power supply for the laser system is 230V-50/60 Hz. The input is 12 A. The whole system has a dimension of 92 cm×33 cm×75 cm, and weighs 80 kg.

The laser settings per treatment are as follows:
Peak Intensity Fluence (PIF): 0.566;
Peak intensity: 19 kW/cm²;
Energy per pulse: 2 Joule;
Repetition frequency: 10 Hz;
Spot size diameter: 10 mm;
Fluence per pulse: 2.54 J/cm²;
Energy per treatment (dose): 2500 J;
Mode: scanning Each subject received a total number of 15 treatment over 3 weeks, on average 5 treatments per week. The treated lesions (HILT group) and the controls (untreated group and healthy group) were subject to histological analysis and/or visual inspection along each step of the treatment (T/0 through T/5).

To assess the effects of HILT we compared histological and immunohistochemical (IHC) findings of the samples collected from the lesion at 30 (T1), 45 (T2) 90 (T3), 120 (T4) and 180 (T5) days later the induction of surgical defect. In particular the samples were stained with H&E, Safranin-O, Alcian Pas and Herovici's stain. Mono and polyclonal antibodies specific to IL-1□, MMP-9, TIMP-2, COMP, IGF-I and collagen types I-II were employed for IHC evaluations.

Results:

The macroscopic observation of the defect areas has showed a progressive re-growth of a new tissue from the edges to the central area of the lesions in Treated group. At T1,2,3 it has been possible to highlight an increase in chondrocytes proliferation and a decrease of inflammatory factors (IL-1□, MMP-9). On the contrary the Untreated group has showed a severe tissue inflammation. At T4 and T5 we observed the formation of a new tissue with some features of hyaline-like cartilage either for the presence of type II collagen expression and for the morphological appearance. We could observe the spatial distribution of collagen fibers according to Benningoff's scheme.

The HILT group had significant cartilage tissue regeneration (re-growth), compared to the untreated group, in which the lesion remained essentially unchanged. Starting from T/3, Safranin O staining showed that the HILT group had similar proteoglycan content in the cartilage compared to healthy cartilage, while the untreated group had minimal proteoglycan staining Immunohistochemistry (IHC) of Type II collagen also showed that the HILT group had similar Type II collagen content compared to healthy cartilage, while the untreated group had minimal staining for Type II collagen. IHC of cartilage oligomeric matrix protein (COMP) showed that the HILT group had significantly more COMP than the untreated group. IHC of typical inflammatory markers (e.g., IL 1β and MMP) showed that the HILT group had significantly lower levels of inflammation than the untreated group. Similar results were obtained at T/4. In addition, at T/4, Alcian PAS stain showed that the HILT group had similar levels of extracellular matrix component and precursors compared to the healthy cartilage, while the untreated group had minimal staining for extracellular matrix or precursors.

At T/5, the HILT group lesion had completely healed visually and microscopically, while the lesion of the untreated group remained unchanged. Safranin O and Alcian PAS stainings showed that the healed area in the HILT group had abundant proteoglycan content and extracellular matrix component and precursors, similar to what is observed of normal cartilage, while the stainings of proteoglycan and extracellular matrix component in the corresponding lesion in the untreated group were minimal. In addition, histochemical stainings of Types I, II and III collagens showed strong stainings in the healed area in the HILT group, similar to what is observed of normal cartilage, while the stainings in the corresponding lesion in the untreated group were minimal.

CT scanning along each stage of the treatment confirmed the re-growth of the cartilage in the HILT group compared to the untreated group.

Discussion:

The non-expression of inflammatory markers (e.g., IL 1β and MMPs) proves that HILT is safe and well tolerated. The over-expression of inflammatory markers in the untreated group is clear evidence of the anti-inflammatory effect of the HILT. Both macroscopic and microscopic pictures show clearly the anabolic effect of HILT. As a result, HILT can stimulate the physiological re-growth of articular cartilage with the same features as the hyaline-like cartilage.

While this invention has been particularly shown and described with references to example embodiments thereof, it will be understood by those skilled in the art that various changes in form and details may be made therein without departing from the scope of the invention encompassed by the appended claims.

What is claimed is:

1. A method for treating selective tissue of a patient, the method comprising:
   generating a pulsed laser beam from a pulsed laser source;
   conveying the pulsed laser beam through an optical fiber into a focusing tip; and
   applying the focusing tip onto the skin of a patient in order to focus the pulsed laser beam in the targeted tissue with a spot having a radius r;
   the pulsed laser beam having a peak intensity fluence (PIF) of 0.1 to 1.0 (J/cm³)² to the tissue, the peak intensity fluence defined by:

$$PIF = I_p \cdot \tau_{on} \cdot \frac{E}{10 \cdot r^3} \cdot \alpha \cdot \frac{\tau_{off}}{(\tau_{on} + \tau_{off})}$$

where $I_p$ is peak intensity of a pulse of the pulsed laser beam, E is energy of the pulse, $\tau_{on}$ is duration of the pulse, $\tau_{off}$ is duration between pulses, and α is water absorption coefficient (cm$^{-1}$) at a wavelength λ of the pulsed laser beam.

2. The method of claim 1, wherein peak power of the pulse is between 400 W and 50 kW, the duration of the pulse is from 1 to 500 microseconds and duty cycle of the pulsed laser beam is from 0.01% to 0.5%.

3. The method of claim 1, wherein the wavelength of the laser beam is between 0.75 and 2.5 micrometers.

4. The method of claim 3 wherein $I_p$ is in the range of 5 kw/cm² to 25 kw/cm², E is in the range of 0.03 to 10 J, $\tau_{on}$ is in the range of 1 to 500 μsec, and duty cycle of the pulsed beam is in the range of 0.01% to 0.5%.

5. The method of claim 4 wherein E is in the range of 0.2 to 2 J.

6. The method of claim 4 wherein λ is in the range of 0.9 to 1.2 micrometers.

7. The method of claim 4 wherein λ is about 1.064 micrometers.

8. The method of claim 4 wherein the step of applying the focusing tip comprises pressing a curved focusing end surface of the focusing tip against the skin.

9. The method of claim 1, wherein the tissue is joint cartilage and the pulsed laser beam stimulates a chondrogenic action on the cartilage.

10. The method of claim 9, wherein the focusing tip focuses the pulsed laser beam to a spot in the tissue at a depth of between about 0.5 centimeter and about 10 centimeters from the surface of the skin.

11. The method of claim 9, wherein the focusing tip includes a cylindrical element and a curved focusing end surface, the cylindrical element being between about 3 cm long and about 4 cm long and having a diameter of between about 1.5 cm and about 2.5 cm, the curved surface having a radius of curvature of between about 10 mm and about 100 mm.

12. The method of claim 9 wherein the step of applying the focusing tip comprises pressing a curved focusing end surface of the focusing tip against the skin.

13. The method of claim 1, wherein the peak power of the pulse, the duration of the pulse and duty cycle of the pulsed laser beam are selected to produce a combined photomechanical and photochemical effect on the tissue.

14. The method of claim 1, wherein the diameter of the spot on the tissue formed by the focusing tip is from 1 millimeter to 20 millimeters.

15. The method of claim 1, further including a step of covering at least a portion of the focusing tip with a gel wherein the gel reduces an optical impedance mismatch between the skin and the focusing tip.

16. The method of claim 1, wherein the step of applying the focusing tip comprises temporarily compressing the skin when applying the treatment.

17. The method of claim 1, wherein a photomechanical effect induced by the pulsed laser beam stimulates a chondrogenic action on the said tissue.

18. The method of claim 1, wherein a photochemical effect induced by the pulsed laser beam controls cell differentiation such that healthy hyaline cartilage tissue is regenerated.

* * * * *